United States Patent
Renninger et al.

(10) Patent No.: US 7,854,774 B2
(45) Date of Patent: Dec. 21, 2010

(54) FUEL COMPONENTS, FUEL COMPOSITIONS AND METHODS OF MAKING AND USING SAME

(75) Inventors: Neil S. Renninger, Oakland, CA (US);
Jack D. Newman, Berkeley, CA (US);
Keith Kinkead Reiling, Oakland, CA (US)

(73) Assignee: Amyris Biotechnologies, Inc., Emeryville, CA (US)

(*) Notice: Subject to any disclaimer, the term of this patent is extended or adjusted under 35 U.S.C. 154(b) by 608 days.

(21) Appl. No.: 11/753,586

(22) Filed: May 25, 2007

(65) Prior Publication Data
US 2008/0092829 A1     Apr. 24, 2008

Related U.S. Application Data

(60) Provisional application No. 60/808,666, filed on May 26, 2006, provisional application No. 60/872,411, filed on Jul. 14, 2006, provisional application No. 60/872,412, filed on Jul. 14, 2006, provisional application No. 60/872,413, filed on Jul. 14, 2006, provisional application No. 60/873,388, filed on Dec. 6, 2006, provisional application No. 60/887,604, filed on Feb. 1, 2007.

(51) Int. Cl.
*C10L 1/18* (2006.01)

(52) U.S. Cl. .............. 44/451; 44/382; 44/369; 44/370; 44/477; 44/385; 44/401

(58) Field of Classification Search .......... 44/350, 44/382, 369, 370, 477, 385, 401, 451; 134/19; 210/209
See application file for complete search history.

(56) References Cited

U.S. PATENT DOCUMENTS

| | | | |
|---|---|---|---|
| 2,308,192 A | 1/1943 | Mikeska et al. |
| 2,988,434 A | 6/1961 | Gottshall et al. |
| 4,081,486 A | 3/1978 | Stapp |
| 4,368,056 A | 1/1983 | Pierce et al. |
| 4,539,014 A | 9/1985 | Sweeney |
| 4,541,836 A | 9/1985 | Derderian |
| 4,541,837 A | 9/1985 | Norton et al. |

(Continued)

FOREIGN PATENT DOCUMENTS

AU     A-22217/83     12/1982

(Continued)

OTHER PUBLICATIONS

English abstract of B6, Jun. 28, 2002, ZAO NPO "Khimsintoz".

(Continued)

*Primary Examiner*—Michael A Marcheschi
*Assistant Examiner*—Chantel Graham
(74) *Attorney, Agent, or Firm*—Jones Day

(57) ABSTRACT

A fuel composition comprises at least a $C_5$ isoprenoid compound or its derivative and a conventional fuel additive. The $C_5$ isoprenoid compound or its derivative can be used as a fuel component or as a fuel additive in the fuel composition. The fuel composition may further comprise a conventional fuel component selected from a diesel fuel, jet fuel, kerosene or gasoline. Methods of making and using the fuel composition are also disclosed.

20 Claims, 20 Drawing Sheets

U.S. PATENT DOCUMENTS

| | | | |
|---|---|---|---|
| 4,713,087 | A | 12/1987 | Jenkins, Jr. et al. |
| 5,362,965 | A | 11/1994 | Maggard |
| 5,938,799 | A | 8/1999 | Spencer et al. |
| 6,090,757 | A | 7/2000 | Steckel |
| 6,179,885 | B1 | 1/2001 | McAtee |
| 6,447,557 | B1 | 9/2002 | Yeh et al. |
| 6,761,745 | B2 | 7/2004 | Hull et al. |
| 7,399,323 | B2 | 7/2008 | Renninger et al. |
| 7,540,888 | B2 | 6/2009 | Ryder et al. |
| 2001/0034966 | A1 | 11/2001 | Golubkov et al. |
| 2004/0060228 | A1 | 4/2004 | Webber |
| 2004/0238006 | A1* | 12/2004 | Sears et al. ............... 134/19 |
| 2005/0009712 | A1 | 1/2005 | Erdemir |
| 2005/0124010 | A1 | 6/2005 | Short et al. |
| 2005/0167351 | A1* | 8/2005 | Herman et al. ............ 210/209 |
| 2009/0272352 | A1 | 11/2009 | Ryder |

FOREIGN PATENT DOCUMENTS

| | | |
|---|---|---|
| CN | 1110306 A | 10/1995 |
| CN | 1119669 A | 4/1996 |
| CN | 1036792 C | 12/1997 |
| CN | 1329130 A | 1/2002 |
| CN | 1465674 A | 1/2004 |
| CN | 1137250 C | 2/2004 |
| CN | 1597877 A | 3/2005 |
| CN | 1687326 A | 10/2005 |
| CN | 1690177 A | 11/2005 |
| CN | 1763157 A | 4/2006 |
| CN | 1800316 A | 7/2006 |
| CN | 1807559 A | 7/2006 |
| CN | 1818029 A | 8/2006 |
| CN | 1818036 A | 8/2006 |
| CN | 1888029 A | 1/2007 |
| EP | 1 589 091 A1 | 10/2005 |
| GB | 2 106 135 A | 4/1983 |
| JP | 2002-265961 | 9/2002 |
| JP | 2003-342589 | 12/2003 |
| RU | 2 212 434 C1 | 6/2002 |
| WO | WO 93/24823 | 12/1993 |
| WO | WO 03/080995 A1 | 10/2003 |

OTHER PUBLICATIONS

English abstract of B8, Dec. 3, 2003, Murota, Wataru, et al.
English abstract of B10, Sep. 18, 2002, Shanin K. K.
English abstract of B12, Aug. 16, 2006, Li, Yinghua, et al.
English abstract of B14, Jul. 26, 2006, Dou, Guanyi.
English abstract of B16, Jul. 12, 2006, Chen, Qingfu.
English abstract of B18, Aug. 16, 2006, Xiao, Jun, et al.
English abstract of B20, Nov. 2, 2005, Li, Yinghua, et al.
English abstract of B22, Oct. 26, 2005, Shandong Normal Universit.
English abstract of B24, Mar. 23, 2005, He, Fengchen.
English abstract of B26, Jan. 7, 2004, Du, Shaoan, et al.
English abstract of B28, Feb. 4, 2004, Duan, Yurong, et al.
English abstract of B30, Jan. 2, 2002, Xie, Xuexiu.
English abstract of B32, Apr. 3, 1996, Xinya Practical Tech.
English abstract of B34, Oct. 18, 1995, Petroleum Conveying Co.
English abstract of B36, Dec. 24, 1997, Du, Shaoan.
English abstract of B38, Jan. 3, 2007, Han, Fusheng.
English abstract of B40, Apr. 26, 2006, Henan Tianguan Ent. Group.
Powell, H. et al.; Contributions to the study of petroleum constitution; Mod. Chem. Ind., Proc. Int. Union Pure Appl. Chem. Symp. (1968), 95-105.; British Petrol. Co. Ltd., L.
Hall, Harry; Assuring the proper product stewardship for the use of ethanol.; World Refining, (Jan.-Feb. 2005) vol. 15, No. 1, pp. 22(5); Access Intelligence, LLC.
Lonnon, David G. et al. ; 17O Quantitative Nuclear Magnetic Resonance Spectroscopy of Gasoline and Oxygenated Additives; Analytical Chemistry (2003), 75(17); Australia.
Demirbas, Ayhan; Conversion of biomass to a pyrolytic oil for blending gasoline; Energy Sources (2001), 23(6), 553-562; Taylor & Francis Ltd.
Karaosmanoglu, F. et al.; The effects of blending agents on alcohol-gasoline fuels; Journal of the Institute of Energy (1993), 66(466), 9-12; Istanbul Tech. Univ., Istanbul.
M. Anwar-ul-Haq; Phase Separation of Methanol/Gasoline Blend. Part II.; Pakistan J. Sci. Ind. Res. vol. 30, No. 11, Nov. 1987, pp. 815; Pakistan.
Karaosmanoglu F et al.; Effects of a new blending agent on ethanol-gasoline fuels; Energy & Fuels V10 N.3 816-20 (May-Jun. 1996); Istanbul Technical University.
Katsuki, Akira et al., Research on a new additive for preventing hob failure caused by water in cutting oil, Bulletin of the JSME (1985), 28(243), 2149-56.
International Search Report, Dated Dec. 6, 2008.
Written Opinion, Dated Dec. 6, 2008.

* cited by examiner

| PROPERTY | UNITS | CARBOB | 3-METHYL-3-BUTEN-1-OL (ISOPRENOL) | | | ISOAMYL ALCOHOL | | | ISOAMYL ALCOHOL (IAOH) | | |
|---|---|---|---|---|---|---|---|---|---|---|---|
| VOL.% | --- | 0 | 9.8 | 13.2 | 17.1 | 10.6 | 14.3 | 18.6 | | | |
| WT.%(OXYGEN CONTENT) | --- | 0 | 2.1 | 2.8 | 3.6 | 2.1 | 2.8 | 3.6 | | | |
| GRAVITY, API | --- | 59.0 | 56.3 | 55.3 | 54.2 | 57.1 | 56.5 | 55.8 | | | |
| OCTANE NUMBER, RESEARCH (RON) | --- | 88.1 | 91.4 | 92.0 | 92.7 | 89.3 | 89.6 | 89.9 | | | |
| OCTANE NUMBER, MOTOR (MON) | --- | 81.1 | 82.5 | 82.9 | 83.3 | 82.0 | 82.4 | 83.1 | | | |
| - ANTI KNOCK INDEX | --- | 84.6 | 87.0 | 87.5 | 88.0 | 85.7 | 86.0 | 86.5 | | | |
| CALC. BLENDING RON | --- | | 121.8 | 117.6 | 115.0 | 99.4 | 98.6 | 97.8 | | | |
| CALC. BLENDING MON | --- | | 95.4 | 94.7 | 94.0 | 89.6 | 90.2 | 91.9 | | | |
| - CALC. BLENDING ANTI KNOCK INDEX | --- | | 108.6 | 106.2 | 104.5 | 94.5 | 94.4 | 94.8 | | | |
| VAPOR PRESSURE (CARB EQUATION) | PSI | 5.71 | 5.45 | 5.35 | 5.22 | 5.35 | 5.35 | 5.18 | | | |
| VAPOR PRESSURE (EPA EQUATION) | PSI | 5.97 | 5.71 | 5.62 | 5.49 | 5.62 | 5.62 | 5.56 | | | |
| VAPOR PRESSURE (ASTM EQUATION) | PSI | 5.83 | 5.57 | 5.47 | 5.35 | 5.47 | 5.47 | 5.42 | | | |
| CALC. BLENDING VAPOR PRESSURE (CARB) | PSI | | 3.1 | 3.0 | 2.8 | 2.3 | 3.2 | 2.9 | | | |
| CALC. BLENDING VAPOR PRESSURE (EPA) | PSI | | 3.3 | 3.3 | 3.2 | 2.7 | 3.5 | 3.8 | | | |
| CALC. BLENDING VAPOR PRESSURE (ASTM) | PSI | | 3.2 | 3.1 | 3.0 | 2.4 | 3.3 | 3.6 | | | |
| NET HEAT OF COMBUSTION | BTU/lb | 18,206 | 17,695 | 17,769 | 17,193 | 17,895 | 18,058 | 17,832 | | | |
| WATER TOLERANCE WITH 10% ETHANOL | °C | <-27 | <-27 | <-27 | <-27 | <-27 | <-27 | <-27 | | | |
| TEMPERATURE V/L | °F | 161.4 | 164.1 | 161.3 | 159.6 | 160.6 | 162.6 | 167.3 | | | |

Fig. 4

| PROPERTY | UNITS | CARBOB | 1-BUTANOL (BuOH) | | | ETHANOL (EtOH) | | | MTBE | ETBE |
|---|---|---|---|---|---|---|---|---|---|---|
| VOL.% | | 0 | 8.9 | 12.0 | 15.6 | 5.7 | 7.7 | 10.0 | 11.0 | 15.0 |
| WT.% (OXYGEN CONTENT) | | 0 | 2.1 | 2.8 | 3.6 | 2.1 | 2.8 | 3.7 | 2.0 | 2.3 |
| GRAVITY, API | --- | 59.0 | 57.3 | 56.9 | 56.3 | 58.4 | 58.2 | 58.0 | 58.8 | 58.8 |
| OCTANE NUMBER, RESEARCH (RON) | --- | 88.1 | 89.4 | 89.9 | 90.1 | 91.1 | 92.1 | 93.3 | 91.8 | 93.8 |
| OCTANE NUMBER, MOTOR (MON) | --- | 81.1 | 81.8 | 82.1 | 82.7 | 83.2 | 84.1 | 84.8 | 84.2 | 85.6 |
| —ANTI KNOCK INDEX | --- | 84.6 | 85.6 | 86.0 | 86.4 | 87.2 | 88.1 | 89.1 | 88.0 | 89.7 |
| CALC. BLENDING RON | --- | | 102.7 | 103.1 | 100.9 | 140.7 | 140.0 | 140.1 | 121.7 | 126.1 |
| CALC. BLENDING MON | --- | | 89.0 | 89.4 | 91.4 | 117.9 | 120.1 | 118.1 | 109.3 | 111.1 |
| —CALC. BLENDING ANTI KNOCK INDEX | --- | | 95.8 | 96.3 | 96.1 | 129.3 | 130.1 | 129.1 | 115.5 | 118.6 |
| VAPOR PRESSURE (CARB EQUATION) | PSI | 5.71 | 6.03 | 5.53 | 5.37 | 7.02 | 7.02 | 7.02 | 6.22 | 5.54 |
| VAPOR PRESSURE (EPA EQUATION) | PSI | 5.97 | 6.28 | 5.78 | 5.63 | 7.25 | 7.25 | 7.25 | 6.48 | 5.80 |
| VAPOR PRESSURE (ASTM EQUATION) | PSI | 5.83 | 6.14 | 5.64 | 5.48 | 7.12 | 7.12 | 7.12 | 6.34 | 5.66 |
| CALC. BLENDING VAPOR PRESSURE (CARB) | PSI | | 9.3 | 4.2 | 3.5 | 28.7 | 22.7 | 18.8 | 10.3 | 4.6 |
| CALC. BLENDING VAPOR PRESSURE (EPA) | PSI | | 9.5 | 4.4 | 3.8 | 28.4 | 22.6 | 18.8 | 10.6 | 4.8 |
| CALC. BLENDING VAPOR PRESSURE (ASTM) | PSI | | 9.3 | 4.2 | 3.6 | 28.5 | 22.6 | 18.7 | 10.5 | 4.7 |
| NET HEAT OF COMBUSTION | BTU/lb | 18,206 | 18,497 | 18,355 | 17,936 | 17,572 | 17,979 | 17,871 | 17,669 | 18,199 |
| WATER TOLERANCE WITH 10% ETHANOL | °C | <-27 | <-27 | <-27 | <-27 | <-27 | <-27 | <-27 | <-27 | <-27 |
| TEMPERATUR V/L | °F | 161.4 | 158.5 | 158.1 | 162.6 | 140.2 | 141.4 | 138.3 | 154.9 | 158.8 |

Fig. 5

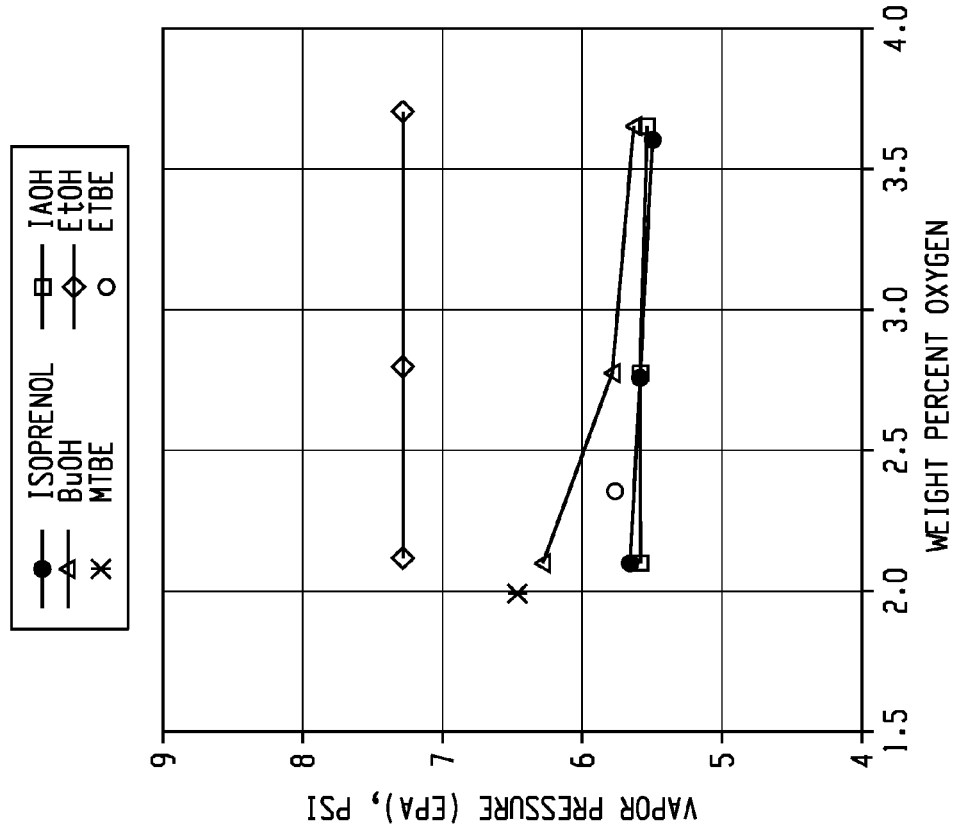
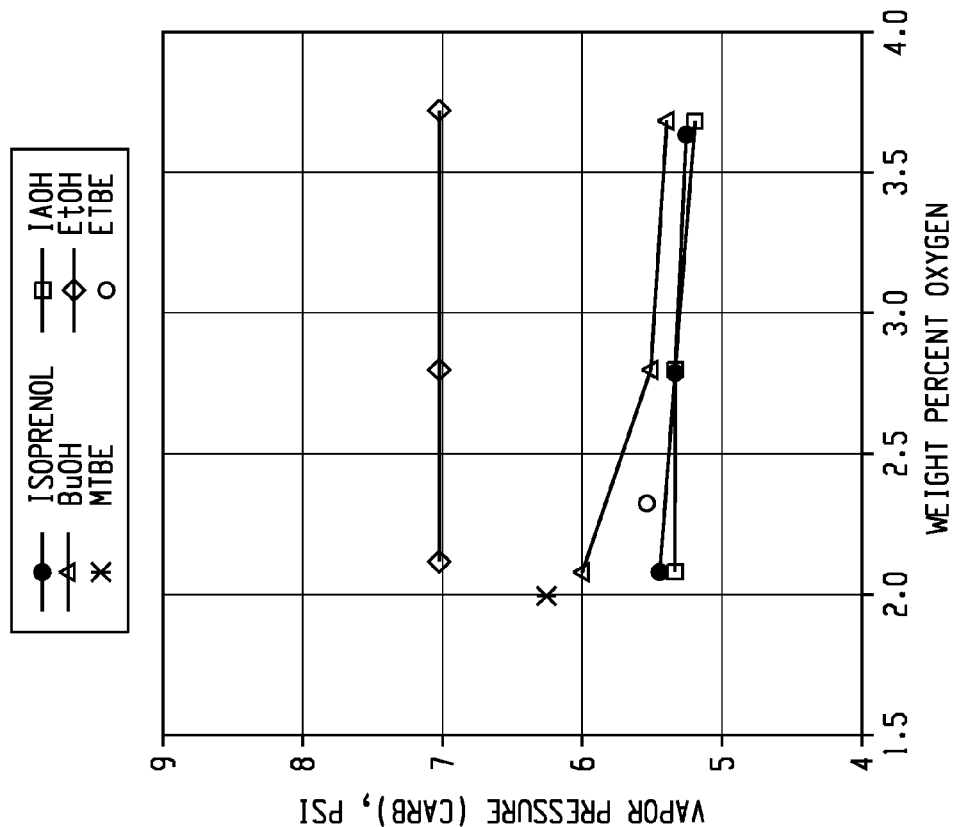

FUEL COMPONENTS, FUEL COMPOSITIONS AND METHODS OF MAKING AND USING SAME

PRIOR RELATED APPLICATIONS

This application claims the benefit under 35 U.S.C. §119(e) of U.S. Provisional Patent Application Nos. 60/808,666, filed May 26, 2006; 60/872,411, filed Jul. 14, 2006; 60/872,412, filed Jul. 14, 2006; 60/872,413, filed Jul. 14, 2006; 60/873,388, filed Dec. 6, 2006; and 60/887,604, filed Feb. 1, 2007, all of which are incorporated herein by reference in their entirety.

FIELD OF THE INVENTION

This invention encompasses, among other things, fuel compositions comprising at least a $C_5$ isoprenoid compound or a derivative thereof and methods of making and using the fuel compositions. In certain embodiments, this invention encompasses fuel compositions comprising 3-methyl-1-butanol (i.e., isoamyl alcohol), 3-methyl-3-buten-1-ol, 3-methyl-2-buten-1-ol or a derivative thereof. In certain embodiments, this invention encompasses a fuel composition utilizing at least a fuel component readily and efficiently produced, at least in part, from a microorganism. In certain embodiments, this invention encompasses a fuel composition comprising a high concentration of at least a bioengineered fuel component.

BACKGROUND OF THE INVENTION

Biofuel is generally a fuel derived from biomass, i.e., recently living organisms or their metabolic byproducts, such as manure from animals. Biofuel is desirable because it is a renewable energy source, unlike other natural resources such as petroleum, coal and nuclear fuels. Biofuel includes, inter alia, biologically produced alcohols, such as methanol, ethanol, propanol and butanol. Generally, such biologically produced alcohols can be formed by the action of microbes and enzymes through fermentation of biomass. For example, methanol can be produced from fermentation of wood or other organic materials or formed naturally in the anaerobic metabolism of many varieties of bacteria. Similarly, ethanol can be mass-produced by fermentation of starch or sugar which can be found in a wide variety of crops such as sugar cane, sugar beet and corn. Furthermore, butanol and ethanol can be produced from starch using *Clostridium acetobutylicum*, a commercially available bacterium, in the A.B.E. (Acetone, Butanol, Ethanol) process. The A.B.E. process was an industry standard before the late 1940's when oil started to become the dominant energy source for its low cost.

Recently, because of concerns over global warming, rising oil prices as well as decreasing oil reserves and increasing political instability in oil producing countries around the world, there are renewed interests from governments, industries and academics in biofuels, particularly biologically produced alcohols. However, methanol, ethanol and propanol are volatile enough that they can cause engine vapor lock and evaporative emission problems. Furthermore, methanol, ethanol and propanol have a high affinity to water and therefore, they generally contain an undesirable amount of water that can cause corrosive problem to internal combustion engines that use them as fuels.

Butanol may be more suited as a biofuel than methanol, ethanol and propanol because the former is less volatile and more hydrophoblic than the latter. However, it is unclear whether the current butanol production methods are economically viable. As a result, there is a need for biofuels that can be produced economically. Further, there is also a need for biofuels that have a low affinity toward water. Further, there is also a need for biofuels that can be made reliably and reproducibly for use in internal combustion engines such as gasoline engines.

SUMMARY OF THE INVENTION

Provided herein are fuel components, fuel compositions and methods of making and using same. Embodiments of the fuel compositions disclosed herein are believed to satisfy the above-mentioned needs. In some embodiments, the fuel compositions comprise one or more $C_5$ isoprenoid compounds or derivatives thereof. In other embodiments, the $C_5$ isoprenoid compounds or derivative thereof can be used as the fuel composition itself, a major component of the fuel composition or a minor component of the fuel composition. In certain embodiments, the $C_5$ isoprenoid compounds or derivatives thereof can be made from microorganisms, including bioengineered microorganisms. In some embodiments, the fuel compositions disclosed herein can be used as gasoline. In further embodiments, the fuel compositions disclosed herein can be used to power internal combustion engines such as gasoline engines.

In one aspect, the invention provides a fuel composition comprising or obtainable from a mixture comprising an isoprenoid compound and a fuel additive. In some embodiments, the isoprenoid compound is represented by formula (Ib) or (Ic):

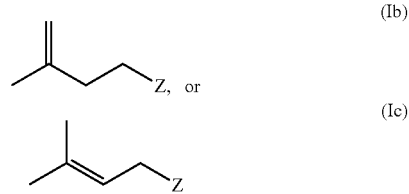

wherein Z is H, O—R, O—C(=O)R, O—PO(OR)$_2$, O—SO$_2$—OR, PO(OR)$_2$ or SO$_2$—OR; and R is H, alkyl, cycloalkyl, aryl, alkaryl or aralkyl. In certain embodiments, the isoprenoid compound is 3-methyl-3-buten-1-ol, i.e., formula (Ib) where Z is OR and R is H. In certain embodiments, the isoprenoid compound is 3-methyl-2-buten-1-ol, i.e., formula (Ic) where Z is OR and R is H. In other embodiments, the isoprenoid compound is in an amount from 2% to 95% by volume, based on the total volume of the fuel composition. In further embodiments, the isoprenoid compound is in an amount of at least 2% by volume, based on the total volume of the fuel composition.

In another aspect, the invention provides a fuel composition comprising or obtainable from a mixture comprising (a) isoamyl alcohol in an amount of at least 35% by weight, based on the total weight of the fuel composition; and (b) a fuel additive.

In some embodiments, the amount of the isoamyl alcohol is at least 30% by volume, at least 40% by volume, or at least 50% by volume, based on the total volume of the fuel composition; or at least 40% by weight or at least 50% by weight, based on the total weight of the fuel composition.

In some embodiments, the fuel composition disclosed herein is free or substantially free of an organic compound which has a spontaneous ignition temperature of less than 450° C., wherein the organic compound is (1) a compound which contains one or more oxygen atoms but no nitrogen atoms; or (2) a compound which contains one or more nitrate groups and one or more ether linkages; or (3) a nitrogen-containing organic compound selected from the group consisting of azo compounds, tetrazines, nitroso compounds, nitro compounds, nitrate compounds, and hyponitrites. In further embodiments, the organic compound is an ether, a peroxide, a hydroperoxide, an aldehyde, an acyl compound, a cyclic ether, an ester, 2-ethoxyethyl nitrate, 2-butoxyethyl nitrate, 2'-butoxy-2-ethoxyethyl nitrate, 2,2-diethoxyethyl nitrate, 1,3-dioxane-5-nitrate, nitromethane, diethylene glycol dinitrate, triethylene glycol dinitrate or the dinitrate of polyethylene glycol of an average molecular weight of 400.

In certain embodiments, the fuel composition disclosed herein is free or substantially free of a second alcohol which is not isoamyl alcohol, 3-methyl-3-buten-1-ol, 3-methyl-2-buten-1-ol or a combination thereof. In further embodiments, the second alcohol is methanol, ethanol, n-propanol, iso-propanol, n-butanol, iso-butanol, tert-butanol, n-pentanol, sec-pentanol, tert-pentanol, n-hexanol, iso-hexanol, sec-hexanol, tert-hexanol, heptanols, octanols, nonanols, decanols or a combination thereof. In some embodiments, the fuel composition disclosed herein is free or substantially free of an aromatic compound. In other embodiments, the fuel composition disclosed herein is free or substantially free of an alkylamine, fatty acid ester or fatty acid salt.

In certain embodiments, the fuel composition disclosed herein further comprises a petroleum-based fuel in an amount from 1% to 95% by volume, based on the total volume of the fuel composition. In some embodiments, the petroleum-based fuel is gasoline. In further embodiments, the $C_5$ isoprenoid compound is according to formula (Ib) and Z is OH and the $C_5$ isoprenoid compound is present in an amount from about 1% to about 5% by volume, from about 1% to about 10% by volume, from about 1% to about 12.5% by volume, from about 2.5% to about 12.5% by volume, or from about 5% to about 12.5% by volume, based on the total volume of the fuel composition.

In certain embodiments, the fuel additive in the fuel composition disclosed herein is selected from the group consisting of oxygenates, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof. In further embodiments, the amount of the fuel additive is from about 0.1% to about 20% by weight or volume, based on the total weight or volume of the fuel composition.

In another aspect, the invention encompasses a vehicle comprising an internal combustion engine; a fuel tank connected to the internal combustion engine; and the fuel composition disclosed herein in the fuel tank, wherein the fuel composition is used to power the internal combustion engine. In some embodiments, the internal combustion engine of the vehicle is a gasoline engine.

In another aspect, the invention encompasses a method of powering an engine comprising the step of combusting a fuel composition disclosed herein.

In another aspect, the invention encompasses a fuel composition comprising a fuel component and a bioengineered $C_5$ isoprenoid compound.

In another aspect, the invention encompasses a fuel composition produced by preparing 3-methyl-3-buten-1-ol using a microorganism, and incorporating the 3-methyl-3-buten-1-ol in a fuel.

In another aspect, the invention encompasses a fuel composition produced by preparing 3-methyl-2-buten-1-ol using a microorganism, and incorporating the 3-methyl-2-buten-1-ol in a fuel.

In another aspect, the invention encompasses a fuel composition produced by preparing 3-methyl-3-buten-1-ol using a microorganism, preparing isoamyl alcohol from the 3-methyl-3-buten-1-ol, and incorporating the isoamyl alcohol in a fuel.

In another aspect, the invention encompasses a fuel composition produced by preparing 3-methyl-2-buten-1-ol using a microorganism, preparing isoamyl alcohol from the 3-methyl-2-buten-1-ol, and incorporating the isoamyl alcohol in a fuel.

In another aspect, the invention encompasses a fuel composition comprising a fuel component or fuel additive derived from a simple sugar. In some embodiments, the invention encompasses a fuel composition wherein the simple sugar is glucose, galactose, mannose, fructose, ribose or a combination thereof.

In another aspect, the invention encompasses a method of making a fuel composition from a simple sugar comprising the steps of:
a) contacting a cell capable of making a $C_5$ isoprenoid compound with the simple sugar under conditions suitable for making the $C_5$ isoprenoid compound; and
c) mixing the $C_5$ isoprenoid compound with one or more fuel components or fuel additives to make the fuel composition.

In another aspect, the invention encompasses a method of making a fuel composition from a simple sugar comprising the steps of:
a) contacting a cell capable of making a $C_5$ isoprenoid starting material with the simple sugar under conditions suitable for making the $C_5$ isoprenoid starting material;
b) hydrogenating the $C_5$ isoprenoid starting material to form a hydrogenated $C_5$ isoprenoid compound; and
c) mixing the hydrogenated $C_5$ isoprenoid compound with one or more fuel components or fuel additives to make the fuel composition.

In another aspect, the invention encompasses a business method comprising the steps of:
(a) obtaining a biofuel comprising at least a $C_5$ alcohol or derivative thereof by performing a fermentation reaction of a sugar with a recombinant host cell, wherein the recombinant host cell produces the $C_5$ alcohol or derivative thereof; and
(b) distributing, marketing or selling the biofuel.

In some embodiments, the recombinant host cell is modified to increase an enzymatic conversion of isopentenyl pyrophosphate (IPP), dimethylallyl pyrophosphate (DMAPP), or a combination thereof to an isopentenol, wherein the recombinant host cell is not a pTRC 99A *E. Coli* strain transformed with a nudF or a yhfR gene.

In other embodiments, the $C_5$ alcohol or derivative thereof is an isoprenoid compound having formula (Ia), (Ib) or (Ic):

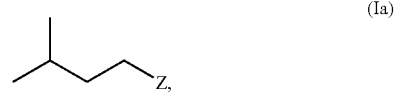

(Ia)

-continued

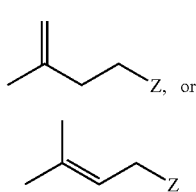

(Ib)

(Ic)

wherein Z is O—R, O—C(=O)R, O—PO(OR)$_2$, O—SO$_2$—OR, PO(OR)$_2$ or SO$_2$—OR; and R is H, alkyl, cycloalkyl, aryl, alkaryl or aralkyl. In further embodiments, when the isoprenoid compound has formula (Ia) where Z is OH, the amount of the isoprenoid compound is at least 30% by volume based on the total volume of the biofuel.

In some embodiments, the amount of the isoprenoid compound is at least 2% by volume based on the total volume of the biofuel.

In certain embodiments, the biofuel comprises 3-methyl-3-buten-1-ol, 3-methyl-2-buten-1-ol, 3-methyl-1-butanol or a combination thereof. In further embodiments, the amount of 3-methyl-3-buten-1-ol, 3-methyl-2-buten-1-ol or 3-methyl-1-butanol is at least about 2%.

In some embodiments, the biofuel further comprises a petroleum-based fuel, a fuel additive or a combination thereof. In further embodiments, the petroleum-based fuel is a gasoline, jet fuel, kerosene, diesel fuel or a combination thereof.

In other embodiments, the fuel additive is selected from the group consisting of oxygenates, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof.

In certain embodiments, the sugar is a simple sugar. In further embodiments, the simple sugar is glucose, galactose, mannose, fructose, ribose or a combination thereof.

DESCRIPTION OF THE DRAWINGS

FIG. 4 shows the API gravity values, research octane numbers, motor octane numbers, anti-knock indexes, vapor pressure data, net heats of combustion, water tolerance data, and vapor-liquid ratio of a California Reformulated Gasoline Blendstock for Oxygen Blending (CARBOB) with no additive and mixtures of CARBOB with various amounts of isoprenol and isoamyl alcohol respectively.

FIG. 5 shows the API gravity values, research octane numbers, motor octane numbers, anti-knock indexes, vapor pressure data, net heats of combustion, water tolerance data, and vapor-liquid ratio of a California Reformulated Gasoline Blendstock for Oxygen Blending (CARBOB) with no additive and mixtures of CARBOB with various amounts of 1-butanol (BuOH), ethanol (EtOH), methyl tertiary-butyl ether (MTBE) and ethyl tertiary-butyl ether (ETBE) respectively.

FIG. 17 shows the vapor pressure values of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content measured by the CARB method.

FIG. 18 shows the vapor pressure values of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content measured by the EPA method.

DEFINITIONS

Figure 1:
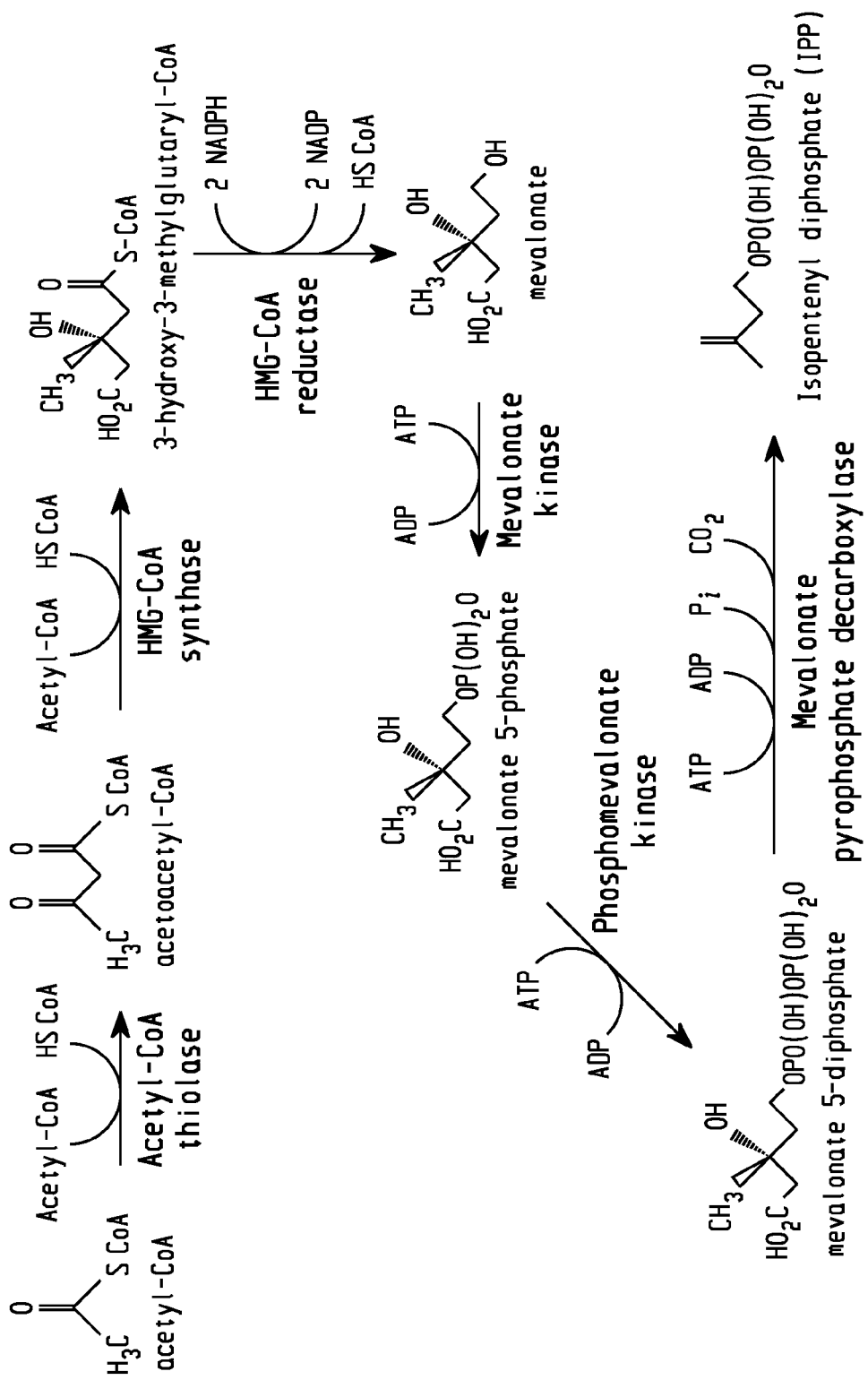
FIG. 1 is a schematic representation of the mevalonate ("MEV") pathway for the production of isopentenyl diphosphate ("IPP").

"Fuel" refers to one or more hydrocarbons, one or more alcohols, one or more fatty esters or a mixture thereof. Preferably, liquid hydrocarbons are used. Fuel can be used to power internal combustion engines such as reciprocating engines (e.g., gasoline engines and diesel engines), Wankel engines, jet engines, some rocket engines, missile engines and gas turbine engines. In some embodiments, fuel typically comprises a mixture of hydrocarbons such as alkanes, cycloalkanes and aromatic hydrocarbons. In other embodiments, fuel comprises one or more of the $C_5$ isoprenoid compounds disclosed herein.

"Fuel composition" is a fuel that comprises at least two fuel components.

"Fuel component" is any compound or a mixture of compounds that are used to formulate a fuel composition. There are "major fuel component" and "minor fuel component." A major fuel component is present in a fuel composition by at least 50% by volume; and a minor fuel component is present in a fuel composition by less than 50%. Fuel additives are minor fuel components. The isoprenoid compounds disclosed herein can be a major component or a minor component, by themselves or in a mixture with other fuel components.

"Bioengineered compound" refers to a compound made by a host cell, including any archae, bacterial, or eukaryotic cells or microorganism.

"$C_5$ isoprenoid starting material" refers to isopentenyl diphosphate ("IPP"), dimethylallyl pyrophosphate (DMAPP) or an unsaturated compound that is capable of being derived from IPP or DMAPP.

"Isoprenoid" and "isoprenoid compound" are used interchangeably herein and refer to a compound derivable from IPP, DMAPP or a combination thereof.

"$C_5$ isoprenoid" or "$C_5$ isoprenoid compound" refers to a $C_5$ hydrocarbon that is capable of being derived from IPP or DMAPP. In certain embodiments, the $C_5$ isoprenoid can be 3-methyl-1-butanol (isoamyl alcohol), or 3-methyl-3-buten-1-ol (isoprenol).

"CARBOB" or "California Reformulated Gasoline Blendstock for Oxygen Blending" refers to the basic blendstock that is produced before an alcohol such as ethanol or a higher alcohol is added to create the finished oxygenated product. In some embodiments, an alcohol is added to CARBOB to form a finished oxygenated product that meets the 2% oxygen requirement. In some embodiments, an alcohol is added to CARBOB to form a finished oxygenated product that meets the 2.7% oxygen requirement. In some embodiments, an alcohol is added to CARBOB to form a finished oxygenated product that meets the 3.5% oxygen requirement.

"API gravity" refers to a specific gravity scale developed by the American Petroleum Institute (API) for measuring the relative density of various petroleum liquids. API gravity can be measured according to ASTM D 1298 or D 4052.

"Research Octane Number" or "RON" refers to the octane number of a fuel determined by running the fuel through a specific test engine with a variable compression ratio under controlled conditions, and comparing these results with those for mixtures of isooctane and n-heptane. RON can be measured according to ASTM D 2699.

"Motor Octane Number" or "MON" refers to the octane number of a fuel determined by running the fuel through a similar test engine to that used in RON testing, but with a preheated fuel mixture, a higher engine speed, and variable ignition timing to further stress the fuel's knock resistance. Depending on the composition of the fuel, the MON of a modern gasoline generally is about 8 to 10 points lower than the RON. MON can be measured according to ASTM D 2700.

"Anti-Knock Index" of a fuel refers to the average of RON and MON of the fuel.

"Vapor pressure" or "Reid vapor pressure" of a gasoline is a measure of the vapor pressure of the gasoline in pounds per square inch at 100° F. It is an indication of the volatility of the gasoline. Reid vapor pressure of a gasoline can be measured according to ASTM D 5191.

"Heat of combustion" of a compound is the energy released as heat when the compound undergoes complete combustion with oxygen. Heat of combustion of a liquid fuel can be measured according to ASTM D4809-95.

Vapor-Liquid Ratio (V/L) of a gasoline refers to the temperature at which the gasoline forms a vapor-liquid ratio of 20 (V/L=20), i.e., the temperature at which it exists as 20 volumes of vapor in equilibrium with one volume of liquid at atmospheric pressure. The temperature for a V/L=20 varies with the season; the normal range is from about 35° C. (95° F.) to about 60° C. (140° F.). Generally, higher values provide greater protection against vapor lock and hot-fuel handling problems. Vapor-Liquid Ratio (V/L) of a liquid fuel can be measured according to ASTM D 2533 or ASTM D 5188.

"Water tolerance with 10 vol. % ethanol test" measures the temperature at which a gasoline-10% alcohol blend separates into two distinct phases. Water tolerance of an oxygenated fuel can be measured according to ASTM D 6422.

"Petroleum-based fuel" means a fuel that includes a fractional distillate of petroleum.

"Jet fuel" refers to a fuel suitable for use in a jet engine.

"Bioengineered fuel" refers to a fuel made by a host cell, including any archae, bacterial, or eukaryotic cells or microorganism.

Biofuel is any fuel that is derived from a biomass, i.e., recently living organisms or their metabolic byproducts, such as manure from cows. It is a renewable energy source, unlike other natural resources such as petroleum, coal and nuclear fuels.

"Fuel additive" refers to chemical components added to fuels to alter the properties of the fuel, e.g., to improve engine performance, fuel handling, fuel stability, or for contaminant control. Types of additives include, but are not limited to, antioxidants, thermal stability improvers, cetane improvers, stabilizers, cold flow improvers, combustion improvers, antifoams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof. The term "conventional additives" refers to fuel additives known to skilled artisan, such as those described above, that are not the $C_5$ isoprenoid compounds disclosed herein.

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol. %, less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

As used herein and unless otherwise indicated, a composition that is "substantially free" of a compound means that the composition contains less than 20 vol. %, less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the compound, based on the total volume of the composition.

As used herein, when the term "group" is used to describe a chemical compound or substituent, the described chemical material includes the basic group and that group with conventional substitution. Where the term "moiety" is used to describe a chemical compound or substituent, only the unsubstituted chemical material is intended to be included. For example, "alkyl group" includes not only such alkyl moieties as methyl ethyl, octyl, stearyl, etc., but also such moieties bearing substituents groups such as alkyl, cycloalkyl, aryl, halogen, cyano, hydroxyl, nitro, amine, carboxylate, etc. On the other hand, "alkyl moiety" or "alkyl" includes only methyl, ethyl, octyl, stearyl, cyclohexyl, etc.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, ..., 50 percent, 51 percent, 52 percent, ..., 95 percent, 96 percent, 97 percent, 98 percent, 99 percent, or 100 percent. Moreover, any numerical range defined by two R numbers as defined in the above is also specifically disclosed.

DESCRIPTION OF EMBODIMENTS OF THE INVENTION

Embodiments of the invention provide fuel compositions comprising at least a $C_5$ isoprenoid compound or a derivative thereof. In certain embodiments, the $C_5$ isoprenoid compound is used as a major fuel component. In other embodiments, the $C_5$ isoprenoid compound is used as minor fuel component in the fuel composition which may further comprise a petroleum-derived fuel component. In further embodiments, the fuel compositions disclosed herein may further comprise at least a conventional fuel additive.

The amount of the $C_5$ isoprenoid compound or a derivative thereof in the fuel composition disclosed herein may be from 0.5% to 99%, from 0.5% to 98%, from 1% to 97%, from 1% to 96%, from 2% to 95%, from 2% to 90%, from 3% to 85%, or from 5% to 80%, based on the total amount of the fuel composition. In certain embodiments, the amount of the $C_5$ cyclic hydrocarbon is more than 1%, more than 2%, more than 3%, more than 4%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90% or more than 95%, based on the total amount of the fuel composition. In some embodiments, the amount is in wt. % based on the total weight of the fuel composition. In other embodiments, the amount is in vol. % based on the total volume of the fuel composition. In certain embodiments, the fuel composition is a gasoline fuel composition.

In some embodiments, the fuel composition comprises or is obtainable from a mixture comprising:

(a) an isoprenoid compound of formula (Ia), (Ib) or (Ic):

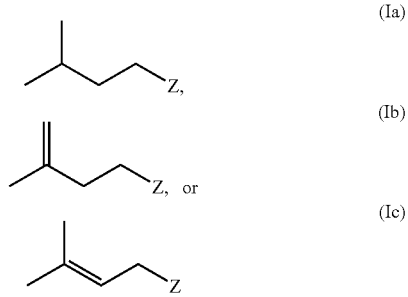

in an amount of at least 2% by volume based on the total volume of the fuel composition, wherein Z is O—R, O—C(=O)R, O—PO(OR)$_2$, O—SO$_2$—OR, PO(OR)$_2$ or SO$_2$—OR; and R is H, alkyl, cycloalkyl, aryl, alkaryl or aralkyl with the proviso that when Z of formula (Ia) is OH, the amount of the isoprenoid compound of formula (Ia) is at least 30% by volume based on the total volume of the fuel composition; and (b) a fuel additive.

In some embodiments, the isoprenoid compound is of formula (Ia) and comprises 3-methyl-1-butanol (CAS 123-51-3; synonyms: isoamyl alcohol and isopentyl alcohol) or 2-methylbutane (CAS 78-78-4; synonyms: isopentane) or a combination thereof. In certain embodiments, the isoprenoid compound of formula (Ia) is or comprises 3-methyl-1-butanol. In other embodiments, the isoprenoid compound of formula (Ia) is or comprises 2-methylbutane.

In some embodiments, the isoprenoid compound is of formula (Ib) or (Ic) and comprises 3-methyl-3-buten-1-ol (CAS 763-32-6; synonyms: 3-isopentyl alcohol and isoprenol) or 3-methyl-2-buten-1-ol (CAS 556-82-1; synonyms: prenyl alcohol and prenol) or a combination thereof. In certain embodiments, the isoprenoid compound of formula (Ib) is or comprises 3-methyl-3-buten-1-ol. In other embodiments, the isoprenoid compound of formula (Ic) is or comprises 3-methyl-2-buten-1-ol.

In some embodiments, the fuel compositions disclosed herein comprise an isoprenoid compound of formula (Ia), (Ib) or (Ic) in an amount between 2% and 95% by volume. In other embodiments, the fuel compositions disclosed herein comprise an isoprenoid compound of formula (Ia) in an amount between 2% and 95% by volume. In some embodiments, the fuel compositions disclosed herein comprise an isoprenoid compound of formula (Ib) in an amount between 2% and 95% by volume. In some embodiments, the fuel compositions disclosed herein comprise an isoprenoid compound of formula (Ic) in an amount between 2% and 95% by volume.

Each of the isoprenoid compounds of formula (Ia), (Ib) or (Ic) in the fuel compositions disclosed herein can function as a fuel component or a fuel additive. In some embodiments, the fuel compositions may further comprise a conventional fuel additive which is discussed below. In other embodiments, the fuel compositions may further comprise a conventional fuel component such as a diesel fuel, a jet fuel, kerosene or gasoline. In further embodiments, the fuel compositions comprise or are obtainable from a mixture comprising at least an isoprenoid compound of formula (Ia), (Ib) or (Ic), at least a conventional fuel component and at least a conventional fuel additive.

In certain embodiments, the isoprenoid compounds of formula (Ia), (Ib) or (Ic) are obtained from bioengineered sources. For example, the bioengineered isoprenoid compounds of formula (Ia), (Ib) or (Ic) can be obtained from a readily available, renewable material. Remarkably, the present invention can provide readily available, renewable sources of energy and methods of their use for the production of energy. In certain embodiments, the bioengineered isoprenoid compounds of formula (Ia), (Ib) or (Ic) can be obtained from a sugar such as monosaccharides (simple sugar), disaccharides and combinations thereof. In certain embodiments, the bioengineered fuel component can be obtained from a simple sugar. In certain embodiments the simple sugar can be any simple sugar capable of supporting the growth of one or more of the cells provided herein. The simple sugar can be any simple sugar known to those of skill in the art. Some non-limiting examples of suitable simple sugars or monosaccharides include glucose, galactose, mannose, fructose, ribose and combinations thereof. Some non-limiting examples of suitable disaccharides include sucrose, lactose, maltose, trehalose, cellobiose and combinations thereof. In certain embodiments, the bioengineered fuel component can be obtained from a polysaccharide. Some non-limiting examples of suitable polysaccharides include starch, glycogen, cellulose, chitin and combinations thereof.

The monosaccharides, disaccharides and polysaccharides suitable for making the bioengineered isoprenoid compounds of formula (Ia), (Ib) or (Ic) can be found in a wide variety of crops or sources. Some non-limiting examples of suitable crops or sources include sugar cane, bagasse, miscanthus, sugar beet, sorghum, grain sorghum, switchgrass, barley, hemp, kenaf, potatoes, sweet potatoes, cassava, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn.

In certain embodiments, the present invention encompasses a fuel composition produced by the methods described herein. In certain embodiments, the present invention encompasses a fuel composition produced by the step of preparing at least an isoprenoid compound of formula (Ia), (Ib) or (Ic) using a microorganism and incorporating the isoprenoid compound in the fuel composition. Methods of preparing the isoprenoid compound using one or more microorganisms are described below. In certain embodiments, the fuel composition is produced by preparing 3-methyl-3-buten-1-ol using one or more microorganisms, preparing 3-methyl-1-butanol from 3-methyl-3-buten-1-ol, and incorporating the 3-methyl-1-butanol in the fuel composition. In other embodiments, the fuel composition is produced by preparing 3-methyl-2-buten-1-ol using one or more microorganisms, preparing 3-methyl-1-butanol from 3-methyl-2-buten-1-ol, and incorporating the 3-methyl-1-butanol in the fuel composition.

In other embodiments, the isoprenoid compound is represented by formula (Ia):

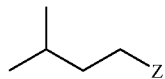

(Ia)

where Z is as defined above.

In one embodiment, the isoprenoid compound of formula (Ia) is or comprises substantially pure 3-methyl-1-butanol having formula (IIa):

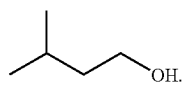

(IIa)

In other embodiments, the isoprenoid compound is represented by formula (Ib):

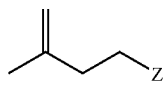

(Ib)

where Z is as defined above.

In one embodiment, the isoprenoid compound of formula (Ib) is or comprises substantially pure 3-methyl-3-buten-1-ol having formula (IIb):

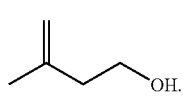

(IIb)

In other embodiments, the isoprenoid compound is represented by formula (Ic):

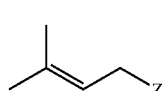

(Ic)

where Z is as defined above.

In one embodiment, the isoprenoid compound of formula (Ic) is or comprises substantially pure 3-methyl-3-buten-1-ol having formula (IIc):

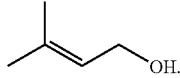

(IIc)

Optionally, the fuel composition disclosed herein may further comprise a petroleum-based fuel component such as conventional gasoline, kerosene, diesel fuel or jet fuel. In some embodiments, the petroleum-based fuel in the fuel composition disclosed herein is gasoline. In certain embodiments, the petroleum-based fuel in the fuel composition disclosed herein is a jet fuel. In further embodiments, the petroleum-based fuel in the fuel composition disclosed herein is kerosene.

The amount of the petroleum-based fuel component in the fuel composition disclosed herein may be from 0.1% to 99%, from 1% to 95%, from 2% to 90%, from 3% to 85%, from 5% to 80%, from 5% to 70%, from 5% to 60%, or from 5% to 50%, based on the total amount of the fuel composition. In certain embodiments, the amount of the petroleum-based fuel component is less than 95%, less than 90%, less than 85%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than 3%, less than 2%, less than 1% or less than 0.5%, based on the total amount of the fuel composition. In some embodiments, the amount is in wt. % based on the total weight of the fuel composition. In other embodiments, the amount is in vol. % based on the total volume of the fuel composition. In certain embodiments, the fuel composition is a gasoline fuel composition.

In some embodiments, the fuel composition comprises at least an isoprenoid compound of formula (Ia), (Ib) or (Ic) and gasoline. In some embodiments, the gasoline meets one or more of the nine gasoline properties as specified in ASTM D 4814 for gasoline, which is incorporated herein by reference. In general, gasoline is a mixture of hydrocarbons whose boiling point is below about 200° C., obtained in the fractional distillation of petroleum. The hydrocarbon constituents in the boiling range of gasoline are generally those that have 4 to 12 carbon atoms in their molecular structure. Gasoline can vary widely in composition; even gasolines with the same octane number may be quite different. For example, low-boiling distillates with high (above 20%) aromatics contents can be obtained from some crude oils. The variation in aromatics content as well as the variation in the content of normal paraffins, branched paraffins, cyclopentanes, and cyclohexanes is dependent upon the characteristics of the petroleum feedstock, and influence the octane number of the gasoline.

The differences in composition of gasoline may require that, in order to produce a uniform product, blending of the products from several component streams may be necessary. The properties of each stream may vary considerably, significantly affecting the product gasoline. The blending process is relatively straightforward, but the determination of the amount of each component to include in a blend is much more difficult.

Volatility is an important property of gasoline and is a necessity to ensure engine starting in cold weather. In winter, volatility is raised and the flash point is lowered by adding the more volatile butanes and pentanes. To prevent vapor lock in warm weather, the amounts of the more volatile constituents are reduced to produce mixtures that will not vaporize in the fuel lines.

In other embodiments, the fuel composition comprises at least an isoprenoid compound of formula (Ia), (Ib) or (Ic) and kerosene. Kerosene in general is a mixture of hydrocarbons, having a boiling point from 285° F. to 610° F. (from 140° C. to 320° C.). It can be used as a fuel or fuel component for jet engines.

In further embodiments, the fuel composition comprises at least an isoprenoid compound of formula (Ia), (Ib) or (Ic) and a jet fuel. Any jet fuel known to skilled artisans can be used herein. The American Society for Testing and Materials ("ASTM") and the United Kingdom Ministry of Defense ("MOD") have taken the lead roles in setting and maintaining specification for civilian aviation turbine fuel or jet fuel. The respective specifications issued by these two organizations are very similar but not identical. Many other countries issue their own national specifications for jet fuel but are very nearly or completely identical to either the ASTM or MOD specification. ASTM D 1655 is the Standard Specification for Aviation Turbine Fuels and includes specifications for Jet A, Jet A-1 and Jet B fuels. Defense Standard 91-91 is the MOD specification for Jet A-1.

The most common jet fuel is a kerosene/paraffin oil-based fuel classified as Jet A-1, which is produced to an internationally standardized set of specifications. In the United States only, a version of Jet A-1 known as Jet A is also used. Another jet fuel that is commonly used in civilian aviation is called Jet B. Jet B is a lighter fuel in the naptha-kerosene region that is used for its enhanced cold-weather performance. Jet A, Jet A-1 and Jet B are specified in ASTM Specification D. 1655-68. Alternatively, jet fuels are classified by militaries around the world with a different system of JP numbers. Some are almost identical to their civilian counterparts and differ only by the amounts of a few additives. For example, Jet A-1 is similar to JP-8 and Jet B is similar to JP-4. Alternatively, jet fuels can also be classified as kerosene or naphtha-type. Some non-limiting examples of kerosene-type jet fuels include Jet A, Jet A1, JP-5 and JP-8. Some non-limiting examples of naphtha-type jets fuels include Jet B and JP-4.

Jet A is used in the United States while most of the rest of the world uses Jet A-1. Jet A is similar to Jet-A1, except for its higher freezing point of −40° C. An important difference between Jet A and Jet A-1 is the maximum freezing point. Jet A-1 has a lower maximum freezing temperature of −47° C. while Jet A has a maximum freezing temperature of −40° C. Like Jet A-1, Jet A has a fairly high flash point of minimum 38° C., with an autoignition temperature of 210° C.

In some embodiments, the fuel composition comprises at least a conventional fuel additive. Some non-limiting examples of fuel additives include oxygenates, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof.

The amount of each of the conventional fuel additives in the fuel composition disclosed herein may be from 0.1% to less than 50%, from 0.2% to 40%, from 0.3% to 30%, from 0.4% to 20%, from 0.5% to 15% or from 0.5% to 10%, based on the total amount of the fuel composition. In certain embodiments, the amount of each of the conventional fuel additives is less than 50%, less than 45%, less than 40%, less than 35%, less than 30%, less than 25%, less than 20%, less than 15%, less than 10%, less than 5%, less than 4%, less than 3%, less than 2%, less than 1% or less than 0.5%, based on the total amount of the fuel composition. In some embodiments, the amount is in wt. % based on the total weight of the fuel composition. In other embodiments, the amount is in vol. % based on the total volume of the fuel composition.

Some conventional fuel additives have been described in "*Gasoline: Additives, Emissions, and Performance*" by Society of Automotive Engineers, SAE International, 1995 (ISBN: 1560916451), which is incorporated herein by reference. Further, the following U.S. patents disclose various fuel additives that can be employed in embodiments of the invention as additives: U.S. Pat. Nos. 6,054,420; 6,051,039; 5,997,593; 5,997,592; 5,993,498; 5,968,211; 5,958,089; 5,931,977; 5,891,203; 5,882,364; 5,880,075; 5,880,072; 5,855,629; 5,853,436; 5,743,922; 5,630,852; 5,529,706; 5,505,867; 5,492,544; 5,490,864; 5,484,462; 5,321,172; and 5,284,492. The disclosures of all of the preceding U.S. patents are incorporated by reference herein in their entirety.

Any oxygenate that increases the weight % of oxygen in the fuel composition disclosed herein can be used. Generally, oxygenates are combustible liquids comprises carbon, hydrogen and oxygen that can be categorized into two classes of organic compounds, i.e., alcohols and ethers. Some non-limiting examples of suitable oxygenates include ethanol, methyl tertiary-butyl ether (MTBE), tertiary-amyl methyl ether (TAME), and ethyl tertiary-butyl ether (ETBE).

Any lubricity improver that increases the fuel lubricity can be used. In some embodiments, one or more lubricity improvers are mixed with the fuel composition disclosed herein. Typically, the concentration of the lubricity improver in the fuel falls in the range of from 1 to 50,000 ppm, preferably about 10 to 20,000 ppm, and more preferably from 25 to 10,000 ppm. Some non-limiting examples of lubricity improver include esters of fatty acids.

Any stabilizer that can improve the storage stability of the fuel composition disclosed herein can be used. Some non-limiting examples of stabilizers include tertiary alkyl primary amines. The stabilizer may be present in the fuel composition at a concentration of about 0.001 to 2 wt %, based on the total weight of the fuel composition, and in one embodiment from 0.01 to 1% by weight.

Any combustion improver that can increase the mass burning rate of the fuel composition disclosed herein can be used. Some non-limiting examples of combustion improvers include ferrocene (dicyclopentadienyl iron), iron-based combustion improvers (e.g., TURBOTECT™ ER-18 from Turbotect (USA) Inc., Tomball, Tex.), barium-based combustion improvers, cerium-based combustion improvers, and iron and magnesium-based combustion improvers (e.g., TURBOTECT™ 703 from Turbotect (USA) Inc., Tomball, Tex.). The combustion improver may be present in the fuel composition at a concentration of about 0.001 to 1 wt %, based on the total weight of the fuel composition, and in one embodiment from 0.01 to 1% by weight.

In some embodiments, the fuel compositions comprise an antioxidant. Any antioxidant that can prevent the formation of gum depositions on fuel system components caused by oxidation of fuels in storage and/or inhibit the formation of peroxide compounds in certain fuel compositions can be used herein. The antioxidant may be present in the fuel composition at a concentration of about 0.001 to 5 wt %, based on the total weight of the fuel composition, and in one embodiment from 0.01 to 1% by weight.

In other embodiments, the fuel compositions comprise a static dissipater. Static dissipaters reduce the effects of static electricity generated by movement of fuel through high flow-rate fuel transfer systems. The static dissipater may be present in the fuel composition at a concentration of about 0.001 to 5 wt %, based on the total weight of the fuel composition, and in one embodiment from 0.01 to 1% by weight.

In further embodiments, the fuel compositions comprise a corrosion inhibitor. Corrosion inhibitors protect ferrous metals in fuel handling systems such as pipelines, and fuel storage tanks, from corrosion. In circumstances where additional lubricity is desired, corrosion inhibitors that also improve the lubricating properties of the composition can be used. The corrosion inhibitor may be present in the fuel composition at a concentration of about 0.001 to 5 wt %, based on the total weight of the fuel composition, and in one embodiment from 0.01 to 1% by weight.

In certain embodiments, the fuel composition comprises a fuel system icing inhibitor (also referred to as an anti-icing additive). Fuel system icing inhibitors reduce the freezing point of water precipitated from jet fuels due to cooling at high altitudes and prevent the formation of ice crystals which restrict the flow of fuel to the engine. Certain fuel system icing inhibitors can also act as a biocide. The fuel system icing inhibitor may be present in the fuel composition at a concentration of about 0.001 to 5 wt %, based on the total weight of the fuel composition, and in one embodiment from 0.01 to 1% by weight.

In another set of embodiments, the fuel compositions further comprise a biocide. Biocides are used to combat microbial growth in the fuel composition. The biocide may be present in the fuel composition at a concentration of about 0.001 to 5 wt %, based on the total weight of the fuel composition, and in one embodiment from 0.01 to 1% by weight.

In another set of embodiments, the fuel composition further comprises a metal deactivator. Metal deactivators suppress the catalytic effect of some metals, particularly copper, have on fuel oxidation. The metal deactivator may be present in the fuel composition at a concentration of about 0.001 to 5 wt %, based on the total weight of the fuel composition, and in one embodiment from 0.01 to 1% by weight.

In another set of embodiments, the fuel composition further comprises a thermal stability improver. Thermal stability improvers are use to inhibit deposit formation in the high temperature areas of the aircraft fuel system. The thermal stability improver may be present in the fuel composition at a concentration of about 0.001 to 5 wt %, based on the total weight of the fuel composition, and in one embodiment from 0.01 to 1% by weight Methods for Making the Inventive Compounds The isoprenoid compound of formula (Ia), (Ib) or (Ic) can be made using any method known in the art including biological methods, chemical syntheses (without the use of biologically derived materials) and hybrid methods where both biological and chemical means are used.

In some embodiments, a hybrid method is used. A $C_5$ isoprenoid starting material is made biologically which is then converted into the desired $C_5$ isoprenoid compound of formula (Ia), (Ib) or (Ic) using chemical synthesis.

Host Cell

A $C_5$ isoprenoid compound or starting material can be made by any method known in the art including biological methods, chemical syntheses, and hybrid methods. When the $C_5$ isoprenoid compound or starting material is made biologically, one method is where a host cell that has been modified to produce the desired product. Like all isoprenoids, a $C_5$ isoprenoid compound or starting material is made biochemically through a common intermediate, isopentenyl diphosphate ("IPP") or dimethylallyl pyrophosphate ("DMAPP").

Any suitable host cell may be used in the practice of the present invention. In one embodiment, the host cell is a genetically modified host microorganism in which nucleic acid molecules have been inserted, deleted or modified (i.e., mutated; e.g., by insertion, deletion, substitution, and/or inversion of nucleotides), to either produce the desired isoprenoid compound or starting material, or increased yields of the desired isoprenoid compound or starting material. In another embodiment, the host cell is capable of being grown in liquid growth medium.

Illustrative examples of suitable host cells include any archae, bacterial, or eukaryotic cell. Examples of an archae cell include, but are not limited to those belong to the genera: *Aeropyrum, Archaeglobus, Halobacterium, Methanococcus, Methanobacterium, Pyrococcus, Sulfolobus*, and *Thermoplasma*. Illustrative examples of archae strains include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum*, and *Thermoplasma volcanium*.

Examples of a bacterial cell include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Illustrative examples of bacterial strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces*, and *Trichoderma*.

Illustrative examples of eukaryotic strains include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Strepto-*

*myces lividans, Streptomyces olivogriseus, Streptomyces rameus, Streptomyces tanashiensis, Streptomyces vinaceus,* and *Trichoderma reesei.*

In general, if a eukaryotic cell is used, a non-pathogenic strain is preferred. Illustrative examples of non-pathogenic strains include but are not limited to: *Fusarium graminearum, Fusarium venenatum, Pichia pastoris, Saccaromyces boulardi,* and *Saccaromyces cerevisiae.*

In addition, certain strains have been designated by the Food and Drug Administration as GRAS or Generally Regarded As Safe. These strains include: *Bacillus subtilis, Lactibacillus acidophilus, Lactobacillus helveticus,* and *Saccharomyces cerevisiae.*

IPP Pathways

There are two known biosynthetic pathways that synthesize IPP and its isomer, dimethylallyl pyrophosphate ("DMAPP"). Eukaryotes other than plants use the mevalonate-dependent ("MEV") isoprenoid pathway exclusively to convert acetyl-coenzyme A ("acetyl-CoA") to IPP, which is subsequently isomerized to DMAPP. Prokaryotes, with some exceptions, use the mevalonate-independent or deoxyxylulose 5-phosphate ("DXP") pathway to produce IPP and DMAPP separately through a branch point. In general, plants use both the MEV and DXP pathways for IPP synthesis.

MEV Pathway

A schematic representation of the MEV pathway is described in FIG. 1. In general, the pathway comprises six steps.

In the first step, two molecules of acetyl-coenzyme A are enzymatically combined to form acetoacetyl-CoA. An enzyme known to catalyze this step is, for example, acetyl-CoA thiolase. Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM-204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP using the mevalonate pathway, then a seventh step is required. An enzyme known to catalyze this step is, for example, IPP isomerase. Illustrative examples of nucleotide sequences include but are not limited to: (NC_000913, 3031087 . . . 3031635; *Escherichia coli*), and (AF082326; *Haematococcus pluvialis*).

DXP Pathway

Figure 2:
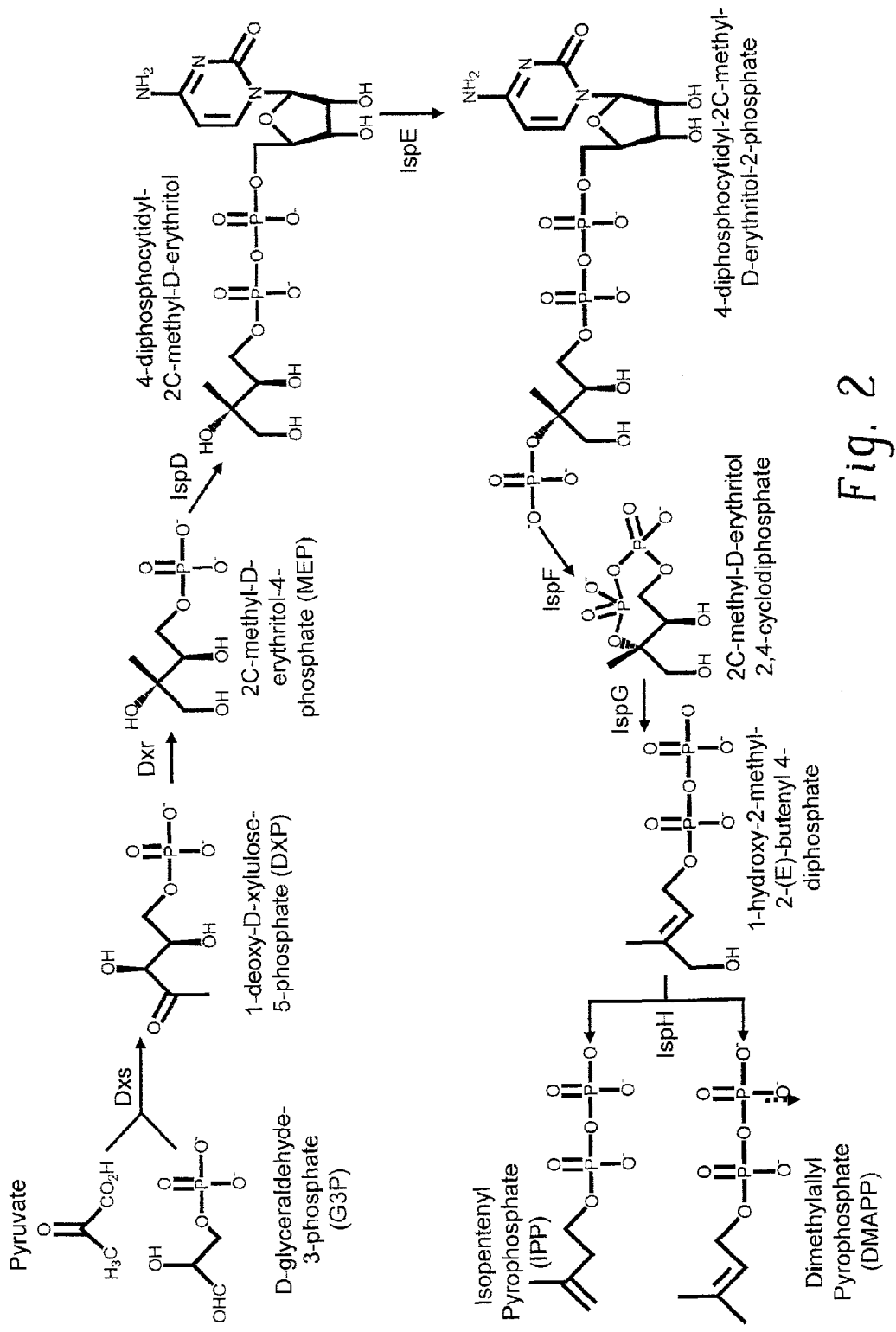
FIG. 2 is a schematic representation of the DXP pathway for the production of IPP and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspE is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 2. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica* Paratyphi, see ATCC 9150), (NC_007493, locus tag RSP_0254; *Rhodobacter* sphaeroides 2.4.1), (NC_005296, locus tag RPA0952; *Rhodopseudomonas palustris* CGA009), (NC_004556, locus tag PD1293; *Xylella fastidiosa* Temecula1), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300;

*Escherichia coli*) and (NC__007493, locus_tag RSP__1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC__007493, locus_tag RSP__6071; *Rhodobacter sphaeroides* 2.4.1), and (NC__002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC__002947, locus_tag PP0853; *Pseudomonas putida* KT2440), and (NC__007493, locus_tag RSP__2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC__002947, locus_tag PP0606; *Pseudomonas putida* KT2440).

In some embodiments, "cross talk" (or interference) between the host cell's own metabolic processes and those processes involved with the production of IPP as provided by the present invention are minimized or eliminated entirely. For example, cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the host cell produces IPP via the DXP pathway, either exclusively or in combination with the MEV pathway. In other embodiments, a host's MEV pathway is functionally disabled so that the host cell produces IPP exclusively through a heterologously introduced DXP pathway. The MEV pathway can be functionally disabled by disabling gene expression or inactivating the function of one or more of the MEV pathway enzymes.

C$_5$ Isoprenoid Compound or Starting Material

IPP or DMAPP is then subsequently converted to various C$_5$ isoprenoid compounds or starting materials using one or more phosphatases as shown in Scheme 1 below.

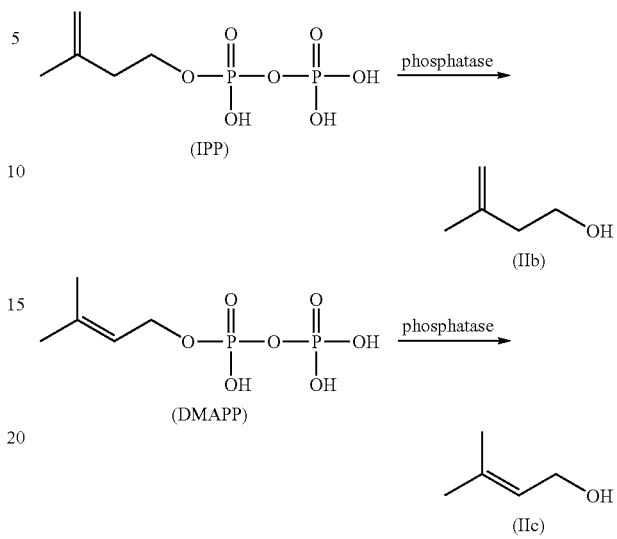

As shown in Scheme 1 above, conversion of IPP or DMAPP to 3-methyl-3-buten-1-ol (Compound (IIb), CAS 763-32-6) or 3-methyl-2-buten-1-ol (Compound (IIc), CAS 556-82-1), respectively, occurs via removal of the terminal pyrophosphate group by a suitable enzyme. Some non-limiting examples of suitable enzymes for catalyzing the conversion of IPP or DMAPP to Compound (IIb) or (IIc) respectively include allyl diphosphatases (Enzyme commission #3.1.7.1), ADP-sugar pyrophosphatases (Enzyme commission #3.6.1.21), ADP-sugar phosphorylases, nucleoside-triphosphate pyrophosphatases (Enzyme commission #3.6.1.19), FAD pyrophosphatases (Enzyme commission #3.6.1.18), monoterpenyl pyrophosphatases Enzyme commission #3.1.7.3), guanosine-3',5'-bis(diphosphate)3'diphosphatases (Enzyme commission #3.1.7.2), alkaline phosphatases (Enzyme commission #3.1.3.1), acid phosphatases (Enzyme commission #3.1.3.2), or other phosphatases classified under enzyme commission classes 3.6.1, 3.1.7, or 3.1.3. Known genes that encode enzymes that can catalyze this conversion include, but are not limited to, the *Bacillus subtilis* 6051 genes nudF and yhfR. The nudF gene product is known to function as an ADP-ribose pyrophosphatase whereas the yhfR gene product has a similar sequence to a phosphoglycerate mutase. Both genes are described as encoding products that can utilize IPP as a substrate in PCT patent publication WO 2005/033287, incorporated herein by reference. The nucleotide sequences for genomic fragments comprising the nudF and yhfR genes are given in SEQ ID NO:11 and SEQ ID NO:12, respectively.

Other suitable enzymes for catalyzing the conversion of IPP and/or DMAPP to Compound (IIb) and/or (IIc) can be identified by introducing a nucleic acid encoding a candidate enzyme into a host test cell, and screening cell extracts derived from a culture of the host test cell for the ability to convert IPP and/or DMAPP to Compound (IIa) and/or (IIc) in vitro. In some embodiments, the nucleic acid is modified (for example, by mutagenizing a cell or organism from which the nucleic acid of interest is subsequently isolated, or by chemical synthesis of a nucleic acid that comprises nucleotide sequence alterations compared to the nucleotide sequence of a known enzyme). In some embodiments, the nucleic acid is a plurality of exogenous nucleic acids (for example, a cDNA or genomic DNA library isolated from a prokaryotic or eukaryotic cell; a population of nucleic acids, each encoding a candidate gene with a different amino acid sequence, etc.), and the nucleic acids are introduced into a plurality of host cells, forming a plurality of test cells. Alternatively, the cell toxicity associated with high level production of IPP can be exploited to identify enzymes that convert IPP and/or DMAPP to Compound (IIb) and/or (IIc), as described in PCT patent publication WO 20051033287.

Chemical Conversion

The isoprenoid compounds of formula (Ia), (Ib) or (Ic):

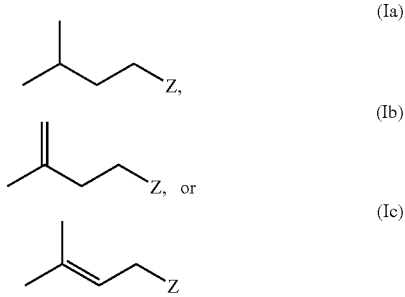

wherein Z is as defined above can be prepared by any method known in the art including biological methods or chemical syntheses (without the use of biologically derived materials) or a combination thereof. In some embodiments, one or more of the above-mentioned $C_5$ isoprenoid compounds or starting materials are isolated from naturally occurring sources which subsequently are converted to the corresponding $C_5$ isoprenoid compounds as shown below.

Irrespective of its source, each of the $C_5$ isoprenoid compounds or starting materials can be chemically converted into a fuel component disclosed herein by any known reduction reaction such as hydrogenation reactions. In some embodiments, the $C_5$ isoprenoid starting material can be reduced by hydrogen with a catalyst such as Pd, Pd/C, Pt, $PtO_2$, $Ru(PPh_3)_2Cl_2$, Raney nickel and combinations thereof. In one embodiment, the catalyst is a Pd catalyst. In another embodiment, the catalyst is 5% Pd/C. In a further embodiment, the catalyst is 10% Pd/C in a high pressure reaction vessel and the reaction is allowed to proceed until completion. Generally, after completion, the reaction mixture can be washed, concentrated, and dried to yield the corresponding hydrogenated product. Alternatively, any reducing agent that can reduce a C=C bond to a C—C bond can also be used. For example, the $C_5$ isoprenoid starting material can be hydrogenated by treatment with hydrazine in the presence of a catalyst, such as 5-ethyl-3-methyllumiflavinium perchlorate, under $O_2$ atmosphere to give the corresponding hydrogenated products. The reduction reaction with hydrazine is disclosed in Imada et al., *J. Am. Chem. Soc.*, 127, 14544-14545 (2005), which is incorporated herein by reference.

In some embodiments, the C=C bonds in the $C_5$ isoprenoid starting materials are reduced to the corresponding C—C bonds by hydrogenation in the presence of a catalyst and hydrogen at room temperature. In certain embodiments, 3-methyl-3-buten-1-ol (formula IIb) or 3-methyl-2-buten-1-ol (formula IIb) is reduced to 3-methyl-1-butanol (formula IIa) by hydrogen in the presence of a 10% Pd/C catalyst as shown in Scheme 2 below.

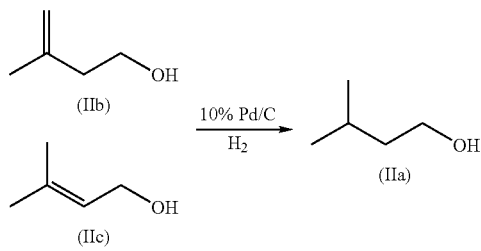

The 3-methyl-1-butanol (i.e., isoamyl alcohol) obtained according to Scheme 2 above can be dehydroxylated to form the corresponding 2-methylbutane or isopentane (CAS 78-78-4) by any known dehydroxylating agent that can dehydroxylate a primary alcohol to the corresponding alkane. In some embodiments, the isoamyl alcohol can be reduced to isopentane by hydrogenation with a nickel-kieselguhr catalyst in the presence of a small amount of thiophene as shown in Scheme 3 below. This hydrogenation reaction is described in Pines et al., *J. Am. Chem. Soc.*, 77, 5099 (1955), which is incorporated herein by reference. In some embodiments, the hydrogenation reaction is carried out at an elevated temperature. In other embodiments, the hydrogenation reaction is carried out at a temperature from 40° C. to 300° C. in an autoclave.

Scheme 3

Alternatively, the isoamyl alcohol can be further modified to produce the corresponding saturated $C_5$ esters by any known esterification agent such as carboxylic acids, carboxylic acid halides (e.g., fluoride, chloride, bromide, and iodide) and carboxylic acid anhydrides. The esterification reactions can be carried out in any reaction conditions recognized by skilled artisans. In some embodiments, the isoamyl alcohol is esterified by reacting it with the desired carboxylic acid in the presence of an acid or a base catalyst, or using either the Fischer or Steglich esterification conditions. In other embodiments, the isoamyl alcohol is esterified by reacting it with the desired carboxylic acid halides in the presence or absence of a base catalyst such as amine and pyridine compounds. In other embodiments, the isoamyl alcohol is esterified by reacting with the desired carboxylic acid anhydrides in the presence of a base catalyst such as amine compounds (e.g., triethylamine), as depicted in Scheme 4 below. The completed reaction mixture can be concentrated, washed, and dried to produce the corresponding ester.

Scheme 4

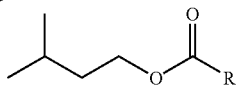

Alternatively, the saturated $C_5$ esters can be obtained from the isoamyl alcohol and a desired ester via a trans-esterification reaction as shown in Scheme 5 below. The trans-esterification reaction can be carried out in any reaction conditions recognized by skilled artisans. In some embodiments, the trans-esterification reaction is catalyzed by a base catalyst such as alkali (e.g., Li, Na, K, Rb and Cs) or alkaline (e.g., Mg, Ca, Sr and Ba) hydroxide, carbonate or acetate, or a combination thereof.

Scheme 5

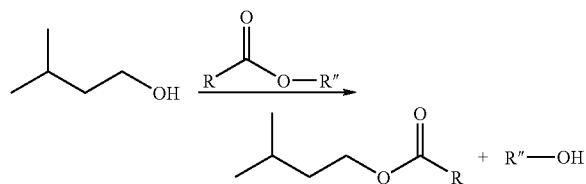

In some embodiments, the isoamyl alcohol can be further modified to produce the corresponding ether by any known alkylating agent such as R—X wherein R is alkyl and X is a good leaving group such as halo, sulfonyl, sulfate group and the like. Some non-limiting examples of the alkylating agent include alkyl halides, alkyl sulfonates and alkyl sulfates. In general, the isoamyl alcohol may be converted to the corresponding alkoxide first by a base and then the $C_5$ alkoxide subsequently react with R—X where X is Cl, Br or I to form the corresponding ethers as shown in Scheme 6 below. In some embodiments, the base can be an active metal such as metallic sodium or a metal hydride such as sodium hydride, lithium aluminum hydride and sodium borohydride.

Scheme 6

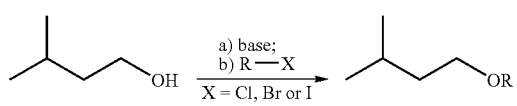

In some embodiments, the isoamyl alcohol can be further modified to produce the corresponding saturated $C_5$ sulfates or sulfonates by any known sulfating or sulfonating agents such as X—S(=O)$_2$Y where Y is H, alkyl, O-alkyl, cycloalkyl, O-cycloalkyl, aryl, O-aryl, alkaryl, O-alkaryl, aryalkyl, and O-aryalkyl; and X is a halide such as F, Cl, Br, and I. Some non-limiting examples of sulfonating agents include alkylsulfonyl halides such as methanesulfonyl chloride, ethanesulfonyl chloride, and 1-propanesulfonyl chloride, cycloalkylsulfonyl halides such as cyclopropanesulfonyl chloride, arylsulfonyl halides such as benzenesulfonyl chloride, aryalkylsulfonyl halides such as phenylmethanesulfonyl chloride, and combinations thereof. Some non-limiting examples of sulfating agents include chlorosulfonic acid, alkyl chlorosulfonate such as methyl chlorosulfonate, n-butyl chlorosulfonate, and 2,2-dimethylpropyl bromosulfonate, aryl chlorosulfonate such as phenyl chlorosulfonate. All of the above mentioned sulfonating agents or sulfating agents can be prepared by known methods or purchased from a commercial supplier such as Aldrich, Milwaukee, Wis. Optionally, the reaction can be carried in the present or absence of a catalyst such as a base catalyst (e.g., amines such as triethylamine).

In certain embodiments, the isoamyl alcohol is sulfated or sulfonated by reacting with the desired sulfonating agents or sulfating agents, as depicted in Scheme 7 below.

Scheme 7

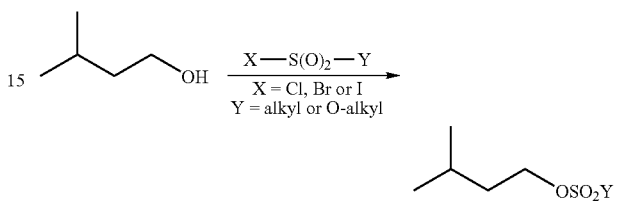

In some embodiments, the isoamyl alcohol can be further modified to produce the corresponding saturated $C_5$ phosphates or phosphonates by any known phosphating or phosphonating agents such as X—P(=O)Y$^1$Y$^2$ where Y$^1$ is alkyl, O-alkyl, cycloalkyl, O-cyclalkyl, aryl, O-aryl, alkaryl, O-alkaryl, aryalkyl, and O-aryalkyl, Y$^2$ is O-alkyl, O-cyclalkyl, O-aryl, O-alkaryl, and O-aryalkyl, and X is a halide such as F, Cl, Br, and I. some non-limiting examples of phosphating agents include dialkyl chlorophosphate such as dimethyl chlorophosphate, diethyl chlorophosphate, and dipentyl chlorophosphate, diaryl chlorophosphate such as diphenyl chlorophosphate, and dialkaryl chlorophosphate such as di-p-tolyl chlorophosphate. some non-limiting examples of phosphonating agents include dialkyl chlorophosphonate such as dimethyl chlorophosphonate, diethyl chlorophosphonate, and diisopropyl chlorophosphonate. All of the above mentioned phosphating or phosphonating agents can be prepared by known methods or purchased from a commercial supplier such as Aldrich, Milwaukee, Wis. Optionally, the reaction can be carried in the present or absence of a catalyst such as a base catalyst (e.g., amines such as triethylamine).

In certain embodiments, the isoamyl alcohol is phosphated or phosphonated by reacting with the desired phosphating or phosphonating agents, as depicted in Scheme 8 below.

Scheme 8

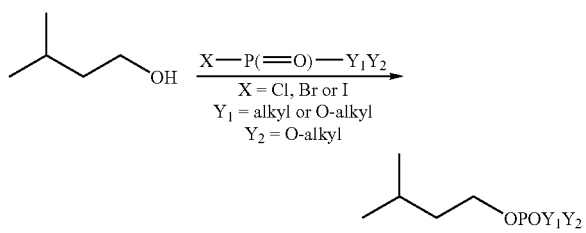

Alternatively, the $C_5$ isoprenoid starting materials, such as 3-methyl-3-buten-1-ol and 3-methyl-2-buten-1-ol, can be first alkylated, esterified, sulfated, phosphated, sulfonated or phosphonated as described above and then subsequently hydrogenated, as depicted in Scheme 9 below where R' is R, C(=O)R, PO(OR)$_2$, SO$_2$—OR, PO(OR)(R$^1$) or SO$_2$—OR; R is H or alkyl and R$^1$ is alkyl.

Scheme 9

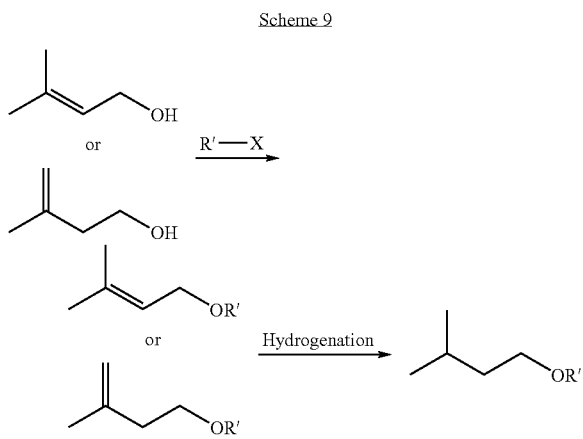

Referring to Scheme 10 below, the esterification of 3-methyl-3-buten-1-ol or 3-methyl-2-buten-1-ol can be carried out in the same manner as described above. The subsequent hydrogenation can be carried out in the same manner as described above. Alternative, the subsequent hydrogenation of the double bonds can be done selectively by using any hydrogenation catalyst that will not affect the —O—C(=O)R group. In some embodiments, the hydrogenation catalyst is Pd/C using diphenylsulfide as a catalyst poison selectively reduces olefin functionalities without hydrogenolysis of the O—C(=O)R group, as disclosed in Mori et al., *Org. Lett.*, 8, 3279-3281 (2006), which is incorporated herein by reference. In other embodiments, poly(ethylene glycol) and Adams' catalyst, i.e., PtO$_2$, can be used as a solvent to selectively hydrogenate the double bonds with hydrogen at 1 atmospheric pressure. The use of the Adams' catalyst is disclosed in Chandrasekhar et al., *J. Org. Chem.*, 71, 2196-2199 (2006), which is incorporated herein by reference.

Scheme 10

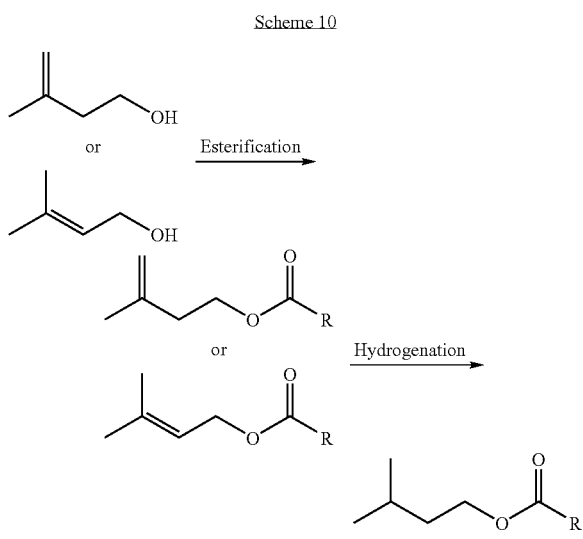

In some embodiments, the 3-methyl-3-buten-1-ol or 3-methyl-2-buten-1-ol can be further modified to produce the corresponding ether by any alkylating agent disclosed herein. In general, the 3-methyl-3-buten-1-ol or 3-methyl-2-buten-1-ol may be converted to the corresponding alkoxide first by a base and then the alkoxide subsequently react with R—X where X is Cl, Br or I to form the corresponding ethers as shown in Scheme 11 below. In some embodiments, the base can be an active metal such as metallic sodium or a metal hydride such as sodium hydride, lithium aluminum hydride and sodium borohydride.

Scheme 11

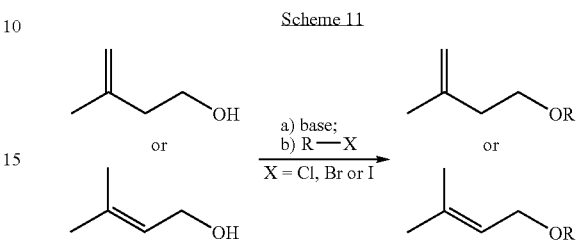

In certain embodiments, the 3-methyl-3-buten-1-ol or 3-methyl-2-buten-1-ol is sulfated or sulfonated by reacting with the desired sulfonating agents or sulfating agents, as depicted in Scheme 12 below.

Scheme 12

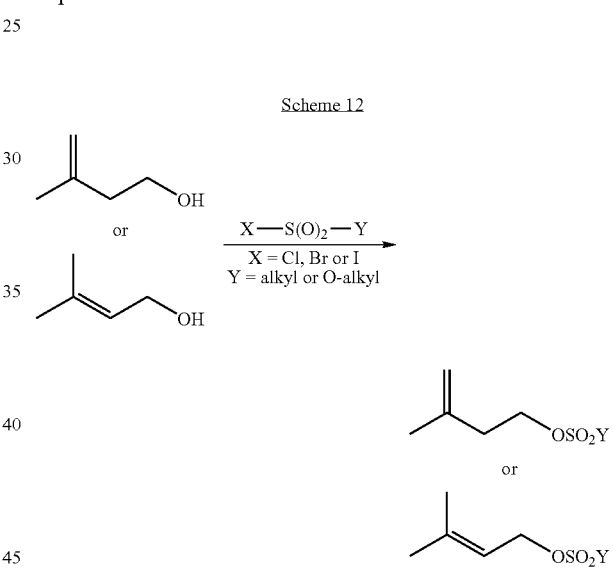

In some embodiments, the 3-methyl-3-buten-1-ol or 3-methyl-2-buten-1-ol can be further modified to produce the corresponding phosphates or phosphonates by any phosphating or phosphonating agents disclosed herein, as depicted in Scheme 13 below. Optionally, the reaction can be carried in the present or absence of a catalyst such as a base catalyst (e.g., amines such as triethylamine).

Scheme 13

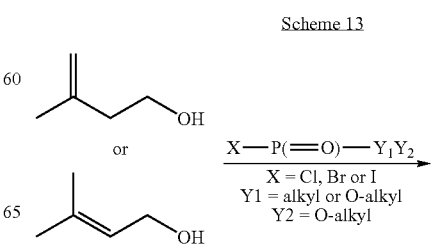

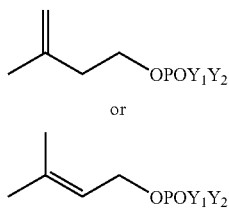

In some embodiments, the $C_5$ isoprenoid starting materials can be converted to isopentane in one step by hydrogenation with a nickel-kieselguhr catalyst in the presence of a small amount of thiophene as shown in Scheme 14 below. In some embodiments, the hydrogenation reaction is carried out at an elevated temperature. In other embodiments, the hydrogenation reaction is carried out at a temperature from 40° C. to 300° C. in an autoclave.

Scheme 14

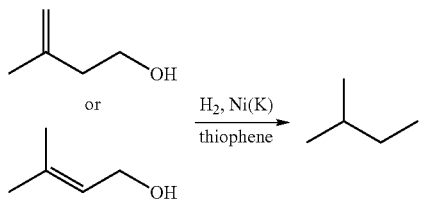

The fuel composition disclosed herein can be used to power any equipment such as an emergency generator or internal combustion engine, which requires a fuel such as jet fuels or missile fuels. An aspect of the present invention provides a fuel system for providing an internal combustion engine with a fuel wherein the fuel system comprises a fuel tank containing the fuel composition disclosed herein. Optionally, the fuel system may further comprise an engine cooling system having a recirculating engine coolant, a fuel line connecting the fuel tank with the internal combustion engine, and/or a fuel filter arranged on the fuel line. Some non-limiting examples of internal combustion engines include reciprocating engines (e.g., gasoline engines and diesel engines), Wankel engines, jet engines, some rocket engines and gas turbine engines.

In some embodiments, the fuel tank is arranged with said cooling system so as to allow heat transfer from the recirculating engine coolant to the fuel composition contained in the fuel tank. In other embodiments, the fuel system further comprises a second fuel tank containing a second fuel for a gasoline engine and a second fuel line connecting the second fuel tank with the internal combustion engine. Optionally, the first and second fuel lines can be provided with electromagnetically operated valves that can be opened or closed independently of each other or simultaneously. In further embodiments, the second fuel is a gasoline.

Another aspect of the invention provides an engine arrangement comprising an internal combustion engine, a fuel tank containing the fuel composition disclosed herein, a fuel line connecting the fuel tank with the internal combustion engine. Optionally, the engine arrangement may further comprise a fuel filter and/or an engine cooling system comprising a recirculating engine coolant. In some embodiments, the internal combustion engine is a gasoline engine. In other embodiments, the internal combustion engine is a jet engine.

When using the fuel composition disclosed herein, it is desirable to remove particulate matter originating from the fuel composition before injecting it into the engine. Therefore, it is desirable to select a suitable fuel filter for use in the fuel system disclosed herein. Water in fuels used in an internal combustion engine, even in small amounts, can be very harmful to the engine. Therefore, it is desirable that water present in fuel composition can be removed prior to injection into the engine. In some embodiments, water and particulate matter can be removed by the use of a fuel filter utilizing a turbine centrifuge, in which water and particulate matter are separated from the fuel composition to an extent allowing injection of the filtrated fuel composition into the engine, without risk of damage to the engine. Other types of fuel filters that can remove water and/or particulate matter may of course also be used.

Another aspect of the invention provides a vehicle comprising an internal combustion engine, a fuel tank containing the fuel composition disclosed herein, a fuel line connecting the fuel tank with the internal combustion engine. Optionally, the vehicle may further comprise a fuel filter and/or an engine cooling system comprising a recirculating engine coolant. Some non-limiting examples of vehicles include cars, motorcycles, trains, ships, and aircraft.

Another aspect of the invention provides a facility for manufacture of a fuel, bioengineered fuel component or bioengineered fuel additive of the invention. In certain embodiments, the facility is capable of biological manufacture of the $C_5$ starting materials. In certain embodiments, the facility is further capable of preparing an isoprenoid fuel component from the starting material.

The facility can comprise any structure useful for preparing the $C_5$ starting material using a microorganism. In some embodiments, the biological facility comprises one or more of the cells disclosed herein. In some embodiments, the biological facility comprises a cell culture comprising at least a $C_5$ starting material in an amount of at least about 1 wt. %, at least about 5 wt. %, at least about 10 wt. %, at least about 20 wt. %, or at least about 30 wt. %, based on the total weight of the cell culture. In further embodiments, the biological facility comprises a fermentor comprising one or more cells described herein.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises a cell culture capable of biologically manufacturing IPP. In further embodiments, the fermentor comprises a cell culture capable of biologically manufacturing DMAPP. In certain embodiments, the fermentor comprises a cell culture comprising at least a $C_5$ starting material in an amount of at least about 1 wt. %, at least about 5 wt. %, at least about 10 wt. %, at least about 20 wt. %, or at least about 30 wt. %, based on the total weight of the cell culture.

The facility can further comprise any structure capable of manufacturing the fuel component or fuel additive from the $C_5$ starting material. The structure may comprise a hydrogenator for the hydrogenation of the $C_5$ starting materials. Any hydrogenator that can be used to reduce C=C double bond to C—C single bonds under conditions known to skilled artisans may be used herein. The hydrogenator may comprise a hydrogenation catalyst disclosed herein. In some embodiments, the structure further comprises a mixer, a container and a mixture of the hydrogenation products from the hydrogenation step and a conventional fuel additive in the container.

Business Methods

One aspect of the present invention relates to a business method comprising: (a) obtaining a biofuel comprising a $C_5$ alcohol or derivative thereof by performing a fermentation reaction of a sugar with a recombinant host cell, wherein the recombinant host cell produces the $C_5$ alcohol or derivative thereof, and (b) marketing and/or selling said biofuel.

In some embodiments, the invention provides a method for competing with petroleum-based fuel and ethanol-based biofuel manufacturers by distributing, selling or offering for sale the biofuels disclosed herein with desirable performance characteristics. The biofuels disclosed herein may be more economical than currently marketed ethanol-based biofuels due to the higher potential yield from sugars, the decreased purification costs, and/or the ease of transport. Further, the biofuels disclosed herein may be higher-performing than currently marketed fuels and ethanol-based biofuels due to potentially higher octane numbers and increased energy contents. Further, the biofuels disclosed herein may be more environmentally-friendly than currently marketed fuels and ethanol-based biofuels due to lower vapor pressures leading to lower evaporative emissions.

In other embodiments, the invention provides a method for marketing or distributing the biofuel disclosed herein to marketers, purveyors, and/or users of a fuel, which method comprises advertising and/or offering for sale the biofuel disclosed herein. In further embodiments, the biofuel disclosed herein may have improved physical or marketing characteristics relative to the natural fuel or ethanol-containing biofuel counterpart.

In certain embodiments, the invention provides a method for partnering or collaborating with or licensing an established petroleum oil refiner to blend the biofuel disclosed herein into petroleum-based fuels such as a gasoline, jet fuel, kerosene, diesel fuel or a combination thereof. In another embodiment, the invention provides a method for partnering or collaborating with or licensing an established petroleum oil refiner to process (for example, hydrogenate, hydrocrack, crack, further purify) the biofuels disclosed herein, thereby modifying them in such a way as to confer properties beneficial to the biofuels. The established petroleum oil refiner can use the biofuel disclosed herein as a feedstock for her chemical modification, the end product of which could be used as a fuel or a blending component of a fuel composition.

In further embodiments, the invention provides a method for partnering or collaborating with or licensing a producer of sugar from a renewable resource (for example, corn, sugar cane, bagass, or lignocellulosic material) to utilize such renewable sugar sources for the production of the biofuels disclosed herein. In some embodiments, corn and sugar cane, the traditional sources of sugar, can be used. In other embodiments, inexpensive lignocellulosic material (agricultural waste, corn stover, or biomass crops such as switchgrass and pampas grass) can be used as a source of sugar. Sugar derived from such inexpensive sources can be fed into the production of the biofuel disclosed herein, in accordance with the methods of the present invention.

In certain embodiments, the invention provides a method for partnering or collaborating with or licensing a chemical producer that produces and/or uses sugar from a renewable resource (for example, corn, sugar cane, bagass, or lignocellulosic material) to utilize sugar obtained from a renewable resource for the production of the biofuel disclosed herein.

EXAMPLES

The following examples are intended for illustrative purposes only and do not limit in any way the scope of the present invention.

Example 1

This example describes methods for making expression plasmids that encode enzymes of the MEV pathway from *Saccharomyces cerevisiae* organized in operons, namely the MevT66, MevB, MBI, and MBIS operons.

Expression plasmid pAM36-MevT66, comprising the MevT66 operon, was generated by inserting the MevT66 operon into the pAM36 vector. The MevT66 operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. Vector pAM36 was generated by inserting an oligonucleotide cassette containing AscI-SfiI-AsiSI-XhoI-PacI-FsII-PmeI restriction enzyme sites into the pACYC184 vector (GenBank accession number XO6403), and by removing the tet resistance gene in pACYC184. The MevT66 operon was synthetically generated using SEQ ID No:1 as a template. The nucleotide sequence comprises the atoB gene from *Escherichia coli* (GenBank accession number NC_000913 REGION: 2324131 . . . 2325315) codon-optimized for expression in *Escherichia coli* (encodes an acetoacetyl-CoA thiolase), the ERG13 gene from *Saccharomyces cerevisiae* (GenBank accession number X96617, REGION: 220 . . . 1695) codon-optimized for expression in *Escherichia coli* (encodes a HMG-CoA synthase), and a truncated version of the HGM1 gene from *Saccharomyces cerevisiae* (GenBank accession number M22002, REGION: 1777 . . . 3285) codon-optimized for expression in *Escherichia coli* (encodes a truncated HMG-CoA reductase). The synthetically generated MevT66 operon was flanked by a 5' EcoRI and a 3' Hind III restriction enzyme site, and could thus be cloned into compatible restriction enzyme sites of a cloning vector such as a standard pUC or pACYC origin vector. The MevT66 operon was PCR amplified with flanking SfiI and AsiSI restriction enzyme sites, the amplified DNA fragment was digested to completion using SfiI and AsiSI restriction enzymes, the reaction mixture was resolved by gel electrophoresis, the approximately 4.2 kb DNA fragment was extracted, and the isolated DNA fragment was inserted into the SfiI and AsiSI restriction enzyme sites of the pAM36 vector, yielding expression plasmid pAM36-MevT66.

Expression plasmid pAM25, also comprising the MevT66 operon, was generated by inserting the MevT66 operon into the pAM29 vector. Vector pAM29 was created by assembling the p15A origin of replication and kan resistance gene from pZS24-MCS1 (Lutz and Bujard *Nucl Acids Res.* 25:1203-1210 (1997)) with an oligonucleotide-generated lacUV5 promoter. The DNA synthesis construct comprising the MevT66 operon (see above) was digested to completion using EcoRI and Hind III restriction enzymes, the reaction mixture was resolved by gel electrophoresis, the 4.2 kb DNA fragment was extracted using a Qiagen gel purification kit (Valencia, Calif.), and the isolated MevT66 operon fragment was inserted into the EcoRI and HindIII restriction enzyme sites of pAM29, yielding expression plasmid pAM25.

Expression plasmid pMevB-Cm, comprising the MevB operon, was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the ERG12 gene (GenBank accession number X55875, REGION: 580 . . . 1911) (encodes a mevalonate kinase), the ERGS gene (GenBank accession number Z49939, REGION: 3363 . . . 4718) (encodes a phosphomevalonate kinase), and the MVD1 gene (GenBank accession number X97557, REGION: 544 . . . 1734) (encodes a mevalonate pyrophosphate carboxylase), and by splicing the genes together using overlap extensions (SOEing). By choosing appropriate primer sequences, the stop codons of ERG12 and ERG8 were changed from TAA to TAG during amplification to introduce ribosome binding sites into the MevB operon. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, and extracting the 4.2 kb DNA fragment. The isolated MevB operon fragment was ligated into the PstI restriction enzyme site of vector pBBR1MCS-1 (Kooach et al., *Gene* 166(1): 175-176 (1995)), yielding expression plasmid pMevB-Cm.

Expression plasmid pMBI, comprising the MBI operon, was generated by inserting the MBI operon into the pBBR1MCS-3 vector. The MBI operon encodes the same enzymes as the MevB operon, as well as an isopentenyl pyrophosphatase isomerase that catalyzes the conversion of IPP to DMAPP. The MBI operon was generated by PCR amplifying the idi gene (GenBank accession number AF119715) from *Escherichia coli* genomic DNA using primers that contained an XmaI restriction enzyme site at their 5 ends, digesting the amplified DNA fragment to completion using XmaI restriction enzyme, resolving the reaction mixture by gel electrophoresis, extracting the 0.5 kb fragment, and ligating the isolated DNA fragment into the XmaI restriction enzyme site of expression plasmid pMevB-Cm, thereby placing idi at the 3' end of the MevB operon and yielding the MBI operon. The MBI operon was subcloned into the SalI and SacI restriction enzyme sites of vector pBBR1-MCS-3, yielding expression plasmid pMBI.

Expression plasmid pMBIS, comprising the MBIS operon, was generated by inserting the ispA gene into pMBI. The ispA gene encodes a farnesyl pyrophosphate synthase that catalyzes the conversion of IPP to DMAPP. The ispA gene (GenBank accession number D00694, REGION: 484 . . . 1383) was PCR amplified from *Escherichia coli* genomic DNA using a forward primer with a SacII restriction enzyme site and a reverse primer with a SacI restriction enzyme site. The amplified PCR product was digested to completion with SacII and SacI restriction enzymes, the reaction mixture was resolved by gel electrophoresis, and the 0.9 kb fragment was extracted. The isolated DNA fragment was ligated into the SacII and SacI restriction enzyme sites of pMBI, thereby placing the ispA gene 3' of idi and the MevB operon, and yielding expression plasmid pMBIS.

Expression plasmid pAM45, comprising both the MevT66 operon and the MBIS operon, was generated by inserting the MBIS operon into pAM36-MevT66 and by adding lacUV5 promoters in front of each operon. The MBIS operon was PCR amplified from pMBIS using primers comprising a 5' XhoI and a 3' PacI restriction enzyme site. The amplified PCR product was digested to completion using XhoI and PacI restriction enzymes, the reaction mixture was resolved by gel electrophoresis, the 5.4 kb DNA fragment was extracted, and the isolated DNA fragment was ligated into the XhoI and PacI restriction enzyme sites of pAM36-MevT66, yielding plasmid pAM43. A nucleotide sequence encoding the lacUV5 promoter was then synthesized from oligonucleotides, and sub-cloned into the AscI SfiI and AsiSI XhoI restriction enzyme sites of pAM43, yielding expression plasmid pAM45.

Example 2

This example describes methods for making expression vectors encoding enzymes of the MEV pathway from *Staphylococcus aureus*.

Expression plasmid pAM41 was derived from expression plasmid pAM25 by replacing the HGM1 nucleotide sequence with the mvaA gene. The mvaA gene encodes the *Staphylococcus aureus* HMG-CoA reductase. The mvaA gene (GenBank accession number BA000017, REGION: 2688925 . . . 2687648) was PCR amplified from *Staphyloccoccus aureus* subsp. *aureus* (ATCC 70069) genomic DNA using primers 4-49 mvaA SpeI (SEQ ID No:2) and 4-49 mvaAR XbaI (SEQ ID No:3), and the amplified DNA fragment was digested to completion using SpeI restriction enzyme, the reaction mixture was resolved by gel electrophoresis, and the approximately 1.3 kb DNA fragment was extracted. The HMG1 nucleotide sequence was removed from pAM25 by digesting the plasmid to completion with HindIII restriction enzyme. The terminal overhangs of the resulting linear DNA fragment were blunted using T4 DNA polymerase. The DNA fragment was then partially digested using SpeI restriction enzyme, the reaction mixture was resolved by gel electrophoresis, and the 4.8 kb DNA fragment was extracted. The isolated DNA fragment was ligated with the SpeI-digested mvaA PCR product, yielding expression plasmid pAM41.

Expression plasmid pAM52 was derived from expression plasmid pAM41 by replacing the ERG13 nucleotide sequence with the mvaS gene. The mvaS gene encodes the *Staphylococcus aureus* HMG-CoA synthase. The mvaS gene (GenBank accession number BA000017, REGION: 2689180 . . . 2690346) was PCR amplified from *Staphyloccoccus aureus* subsp. *aureus* (ATCC 70069) genomic DNA using primers HMGS 5' Sa mvaS-S (SEQ ID No:4) and HMGS 3' Sa mvaS-AS (SEQ ID No:5), and the amplified DNA fragment was used as a PCR primer to replace the HMG1 gene in pAM41 according to the method of Geiser et al. *BioTechniques* 31:88-92 (2001), yielding expression plasmid pAM52.

Expression plasmid pAM97 was derived from expression plasmid pAM45 by replacing the MevT66 operon with the (atoB(opt):mvaA:mvaS) operon of expression plasmid pAM52. Expression plasmid pAM45 was digested to completion using AsiSI and SfiI restriction enzymes, the reaction mixture was resolved by gel electrophoresis, and the 8.3 kb DNA fragment lacking the MevT66 operon was extracted. The (atoB(opt):mvaA:mvaS) operon of pAM52 was PCR amplified using primers 19-25 atoB SfiI-S (SEQ ID No:6) and 19-25 mvaA-AsiSI-AS (SEQ ID No:7), the PCR product was digested to completion using SfiI and AsiSI restriction enzymes, the reaction mixture was resolved by gel electrophoresis, and the 3.7 kb DNA fragment was extracted. The isolated DNA fragment was ligated into the AsiSI and SfiI restriction enzyme sites of expression plasmid pAM45, yielding expression plasmid pAM97.

Expression plasmid pAM97-MBI was derived from expression plasmid pAM97 and pAM45 by replacing the MBIS operon of pAM97 with the MBI operon of pAM45. The MBI operon was PCR amplified from pAM45 using primers 9-70C (SEQ ID No:8) and 26-39B (SEQ ID No:9), the reaction mixture was resolved by gel electrophoresis, the 4.5 kb DNA fragment was extracted, and the isolated DNA fragment was digested to completion using SacI and X XhoI restriction enzymes. Expression plasmid pAM97 was digested to completion using SacI and XhoI restriction enzymes, the reaction mixture was resolved by gel electrophoresis, the 7.6 kb fragment was extracted, and the isolated DNA fragment was ligated with the MBI operon PCR product, yielding expression plasmid pAM97-MBI.

Expression plasmid pAM97-MevB was derived from expression plasmid pAM97 and pAM45 by replacing the MBIS operon of pAM97 with the MevB operon of pAM45. The MevB operon was PCR amplified from pAM45 using primers 9-70C (SEQ ID No:8) and 26-39A (SEQ ID No:10), the reaction mixture was resolved by gel electrophoresis, the 3.9 kb DNA fragment was extracted, and the isolated DNA fragment was digested to completion using SacI and XhoI restriction enzymes. Expression plasmid pAM97 was digested to completion using SacI and XhoI restriction enzymes, the reaction mixture was resolved by gel electrophoresis, the 7.6 kb fragment was extracted, and the isolated DNA fragment was ligated with the MevB operon PCR product, yielding expression plasmid pAM97-MevB.

Example 3

This example describes the generation of *Escherichia coli* host strains for the production of 3-methyl-but-3-en-1-ol and 3-methyl-but-2-en-1-ol. Host strain B286 was created by transforming chemically competent *Escherichia coli* DH1 cells with expression plasmids pAM97-MevB and pC9. Host strain B287 was created by transforming chemically competent *Escherichia coli* DH1 cells with expression plasmids pAM97-MevB and pnudF-H. Host strain B288 was created by transforming chemically competent *Escherichia coli* DH1 cells with expression plasmids pAM97-MevB and pyhfR. Host strain B291 was created by transforming chemically competent *Escherichia coli* DH1 cells with expression plasmids pAM97-MBI and pyhfR.

Expression plasmid pC9 was generated by inserting a genomic DNA fragment of *Bacillus subtilis* 6051 comprising the coding sequence of the nudF gene and upstream genomic sequences (SEQ ID No:11) into vector pTrc99A (GenBank accession number H22744). Expression plasmid pNudF-H was generated by inserting the coding sequence of the *Bacillus subtilis* 6051 nudF gene into vector pTrc99A. Expression plasmid pyhfR was generated by inserting the coding sequence of the *Bacillus subtilis* 6051 yhfR gene (SEQ ID No:12) into vector pTrc99A.

Host cell transformants were selected on Luria-Bertoni (LB) media containing 100 ug/mL carbenicillin and 34 ug/mL chloramphenicol. Single colonies were transferred from the LB agar plate to culture tubes containing 5 mL of LB liquid medium and antibiotics as detailed above. The cultures were incubated by shaking at 37° C. until growth reached stationary phase. The cells were stored at −80° C. in cryovials in 1 mL frozen aliquots made up of 400 uL 50% glycerol and 600 uL liquid culture.

Example 4

This example describes the production of 3-methyl-but-3-en-1-ol and 3-methyl-but-2-en-1-ol in an *Escherichia coli* host strain of Example 3.

For each of the three strains, a frozen working stock was streaked out on an LB agar plate containing 100 ug/mL carbenicillin and 34 ug/mL chloramphenicol. For each strain, three independent colonies were picked, and each colony was used to inoculate a culture tube containing 7 mL of LB broth with antibiotics. The cultures were grown overnight by shaking at 37° C. on a rotary shaker at 250 rpm. At an $OD_{600}$ of 0.2 the cultures were transferred into a 250 mL flask containing 40 ml of M9-Mops, 2% glucose, 0.5% Yeast extract, and antibiotics as detailed above. The cultures were grown by shaking at 30° C. and 250 rpm for 72 hours. When the cultures reached an $OD_{600}$ of 0.35 to 0.45, they were induced with 0.25 mM IPTG. Twice a day, the $OD_{600}$ of each culture was measured, and a 700 uL sample was removed. To 300 uL of each removed sample, 600 uL of ethyl acetate were added, and the sample was vortexed for 15 minutes. 400 uL of the upper ethyl acetate phase was transferred to a clean glass vial for analysis by gas chromatography-mass spectrometry.

The samples were analyzed on a Hewlett-Packard 6890 gas chromatograph/mass spectrometer (GC/MS). A 1 uL sample was separated on the GC using a DB-5 column (Agilent Technologies, Inc., Palo Alto, Calif.) and helium carrier gas. The oven cycle for each sample was 60° C. for 3 minutes, increasing temperature at 60° C./minute to a temperature of 300° C., and a hold at 300° C. for 2 minutes. The total run time was 9 minutes. The resolved samples were analyzed by a Hewlett-Packard model 5973 mass selective detector. Previous mass spectra demonstrated that 3-methyl-3-buten-1-ol and 3-methyl-2-buten-1-ol have a retention time of 2.067 minutes using this GC protocol. To focus detection on 3-methyl-3-buten-1-ol and 3-methyl-2-buten-1-ol, a selective-ion-monitoring method was employed that monitors only ions 56 and 68 in 3-methyl-3-buten-1-ol and 3-methyl-2-buten-1-ol.

Figure 3:
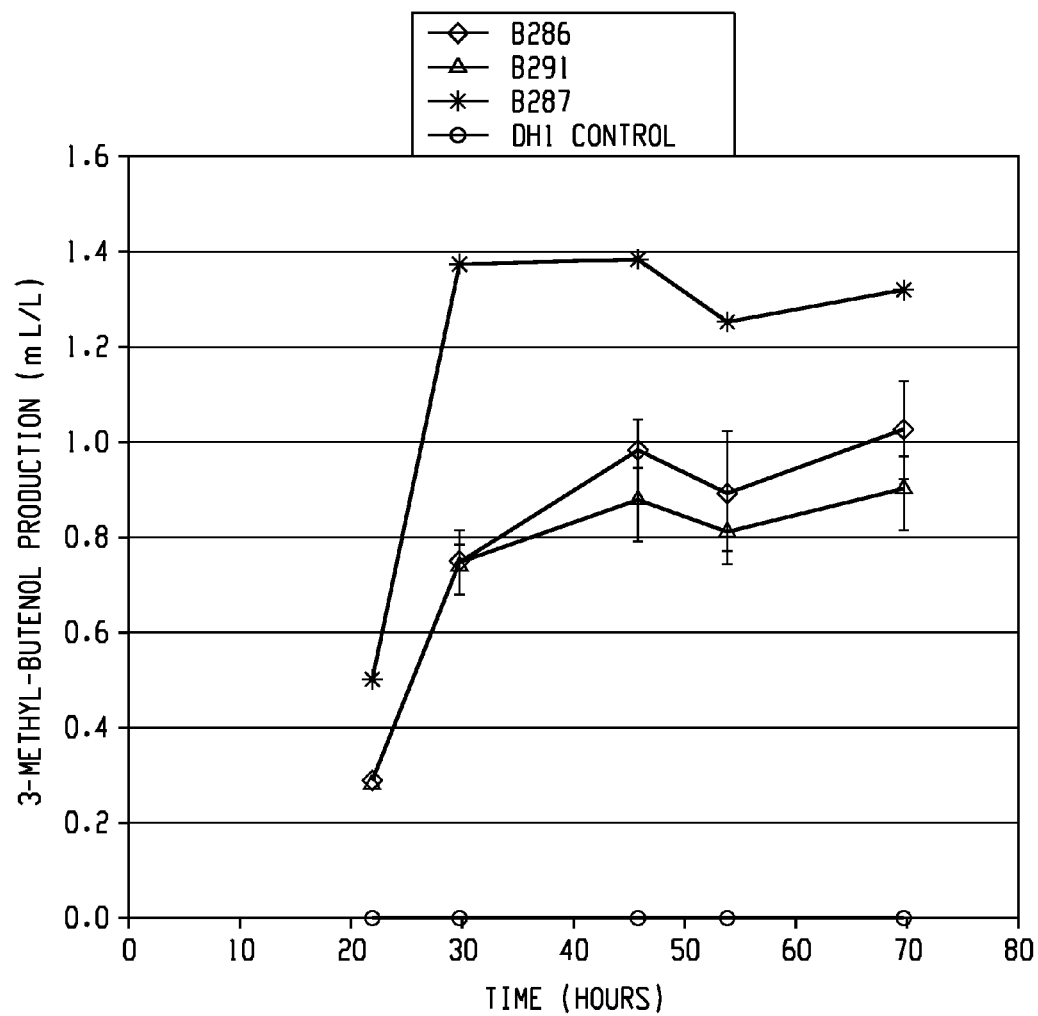
FIG. 3 shows relative production levels of 3-methyl-3-buten-1-ol or 3-methyl-2-buten-1-ol by strains DH1 (untransformed control; represented by open circles), B286 (represented by open diamonds), B287 (represented by *'s), and B291 (represented by open triangles).
Figure 6:
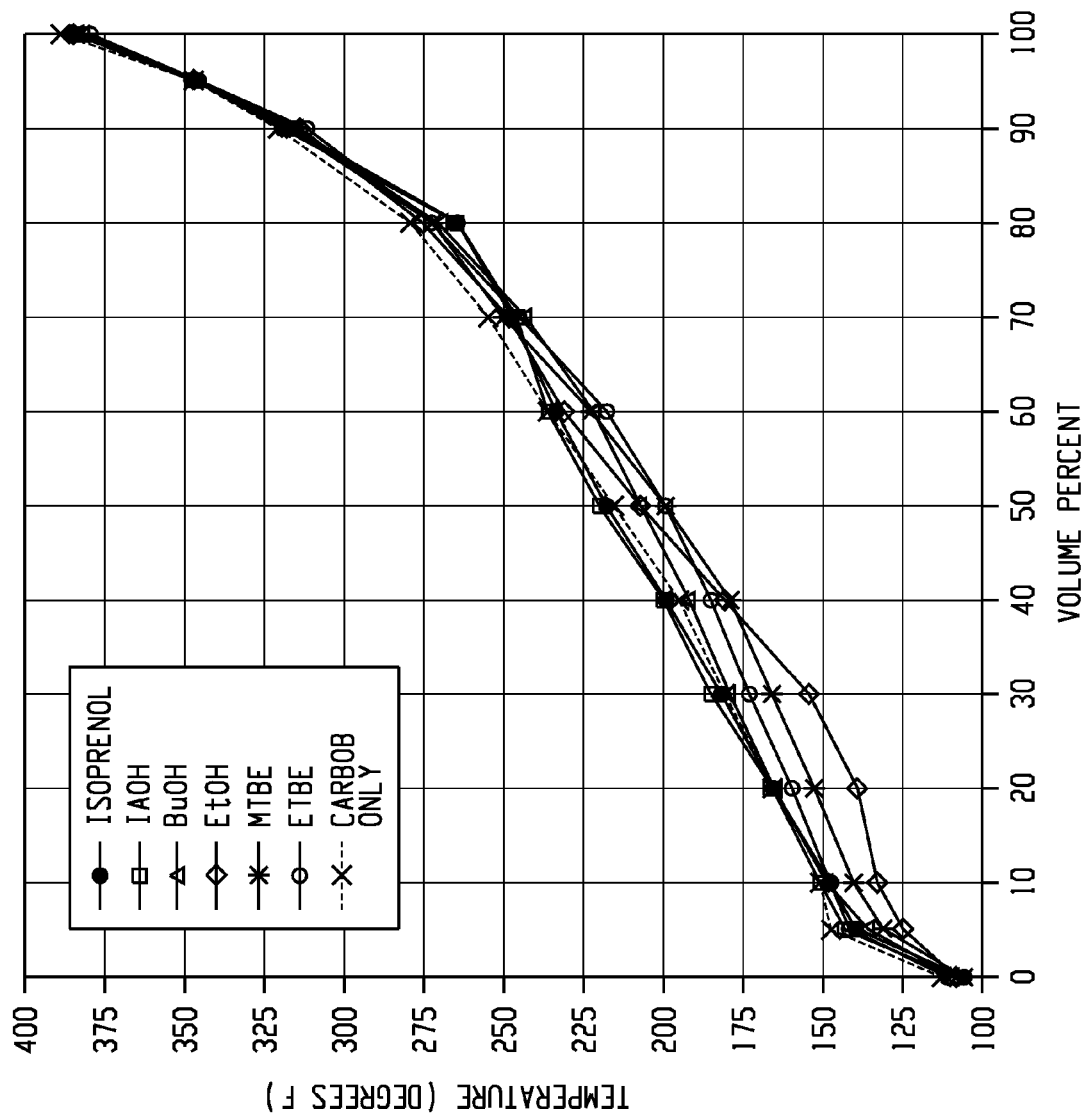
FIG. 6 shows the distillation curves for CARBOB (represented by X's) and mixtures of CARBOB and isoprenol (i.e., 3-methyl-3-buten-1-ol or 3-methyl-2-buten-1-ol; represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at approximately 2.0-2.3 wt. % oxygen content.
Figure 7:
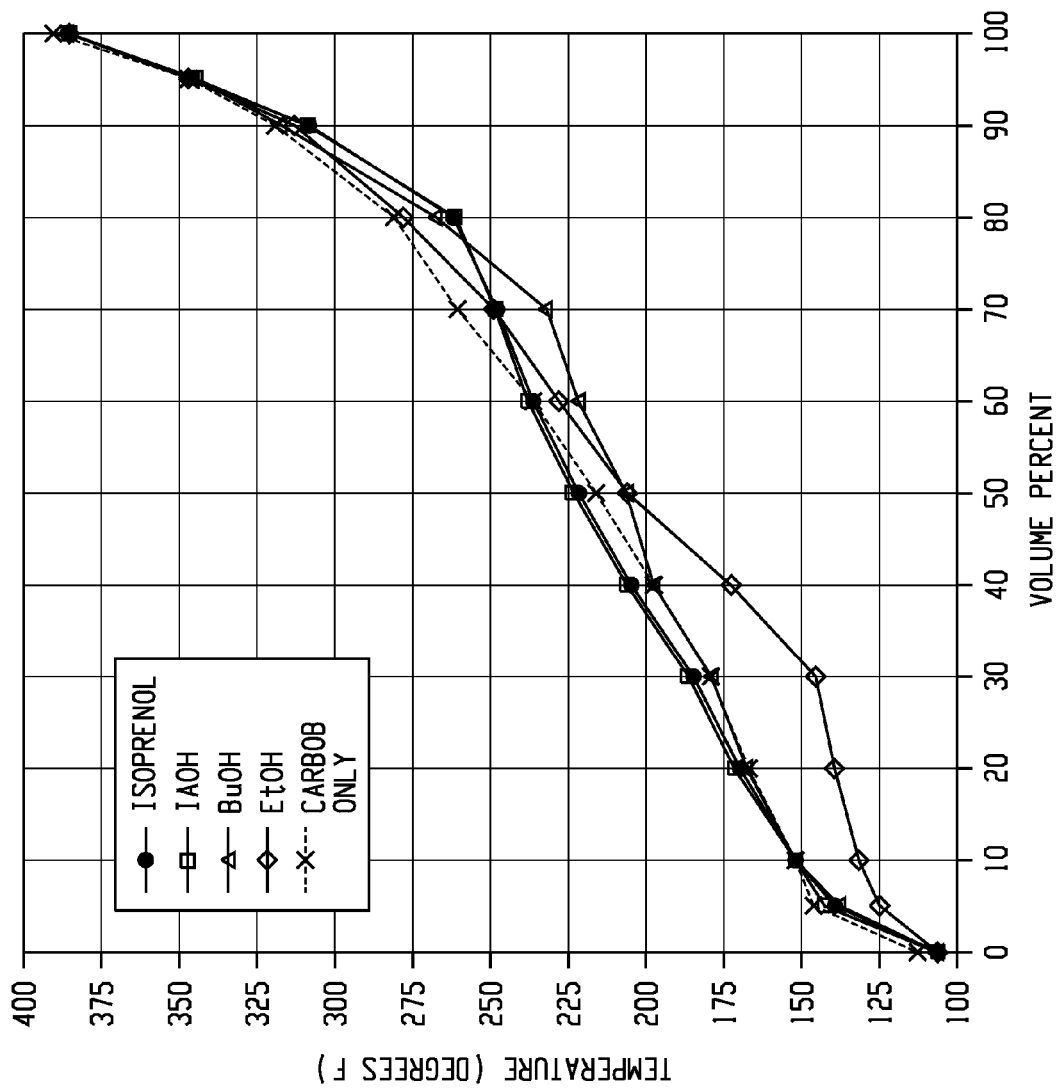
FIG. 7 shows the distillation curves for CARBOB (represented by X's) and mixtures of CARBOB and isoprenol (represented by solid circles), isoamyl alcohol (IAOH; represented by open squares), 1-butanol (BuOH; represented by open triangles) and ethanol (EtOH; represented by open diamonds) respectively at approximately 2.8 wt. % oxygen content.
Figure 8:
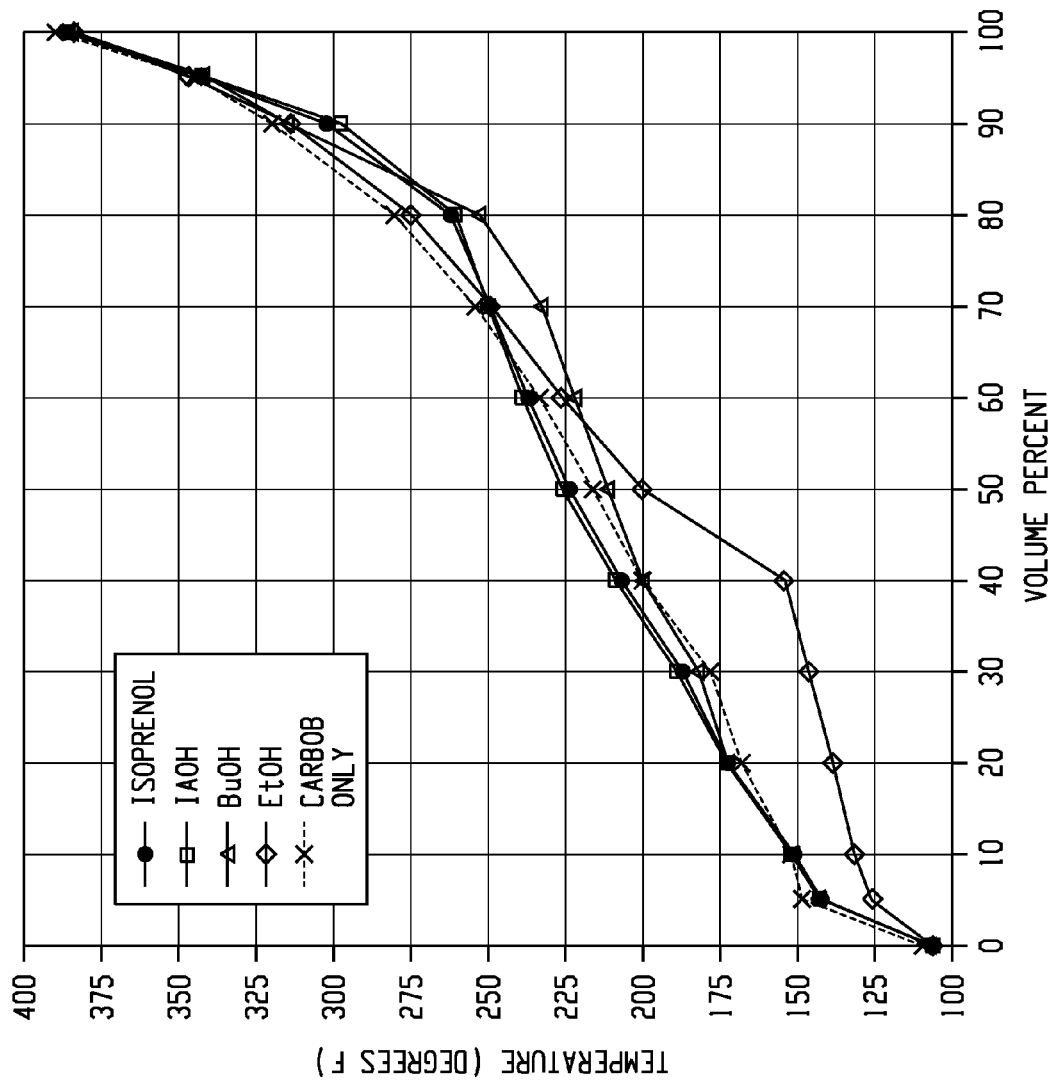
FIG. 8 shows the distillation curves for CARBOB (represented by X's) and mixtures of CARBOB and isoprenol (represented by solid circles), isoamyl alcohol (IAOH; represented by open squares), 1-butanol (BuOH; represented by open triangles) and ethanol (EtOH; represented by open diamonds) respectively at approximately 3.6-3.7 wt. % oxygen content.
Figure 9:
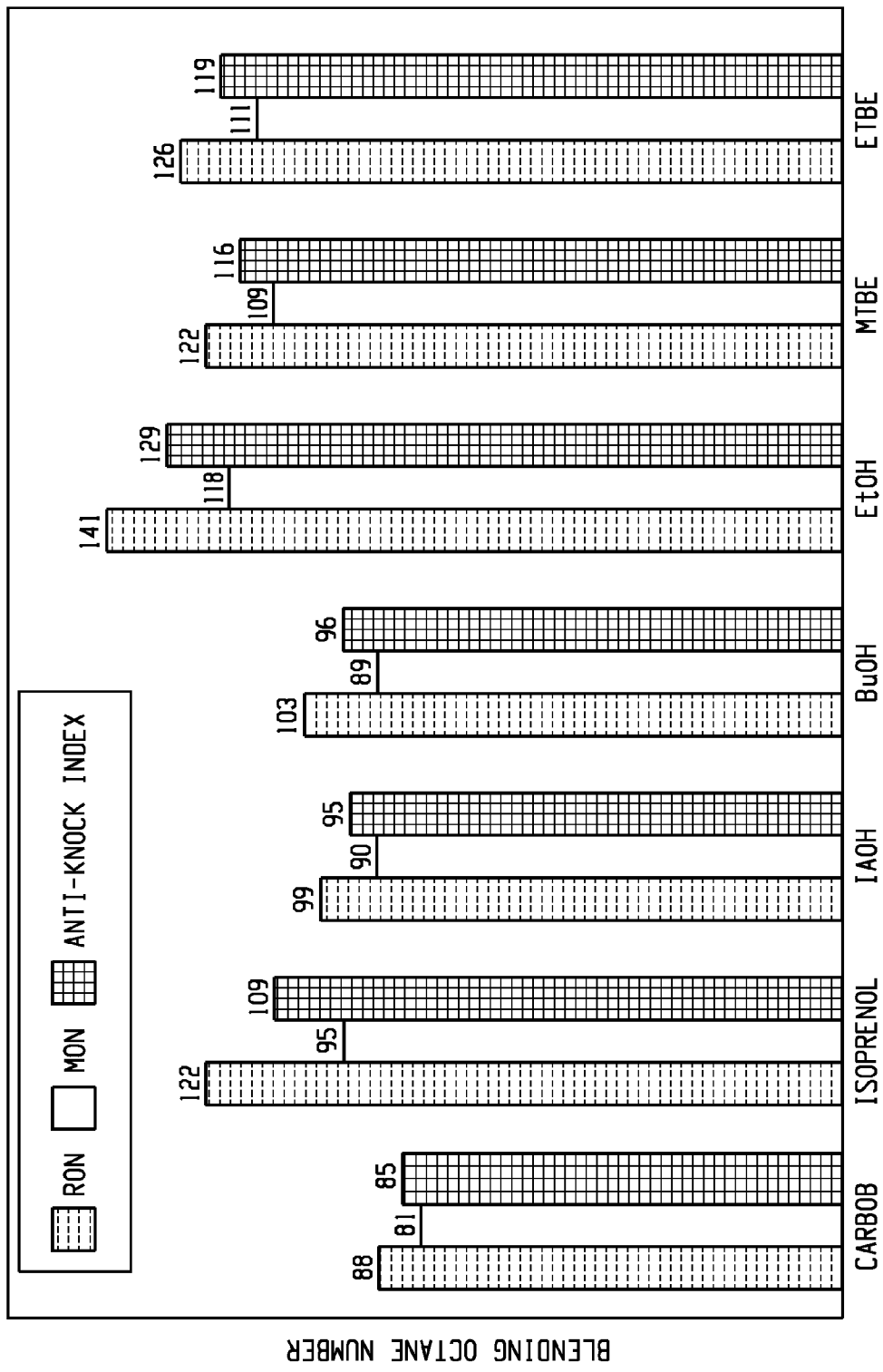
FIG. 9 shows the research octane numbers (RON; represented by bars with short dashes), motor octane numbers (MON; represented by white bars), and anti-knock indexes (represented by bars with squares) of CARBOB and mixtures of CARBOB and isoprenol, isoamyl alcohol (IAOH), 1-butanol (BuOH), ethanol (EtOH), methyl tertiary-butyl ether (MTBE) and ethyl tertiary-butyl ether (ETBE) respectively at approximately 2 wt. % oxygen content.
Figure 11:
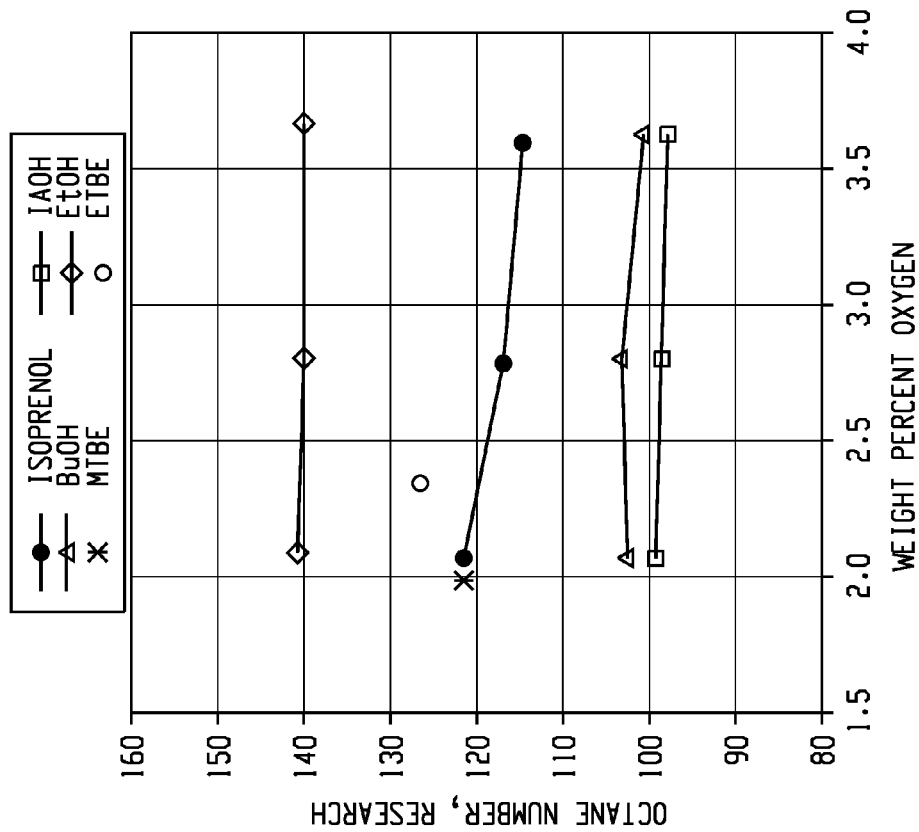
FIG. 11 shows the research octane numbers (RON) of isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
Figure 10:
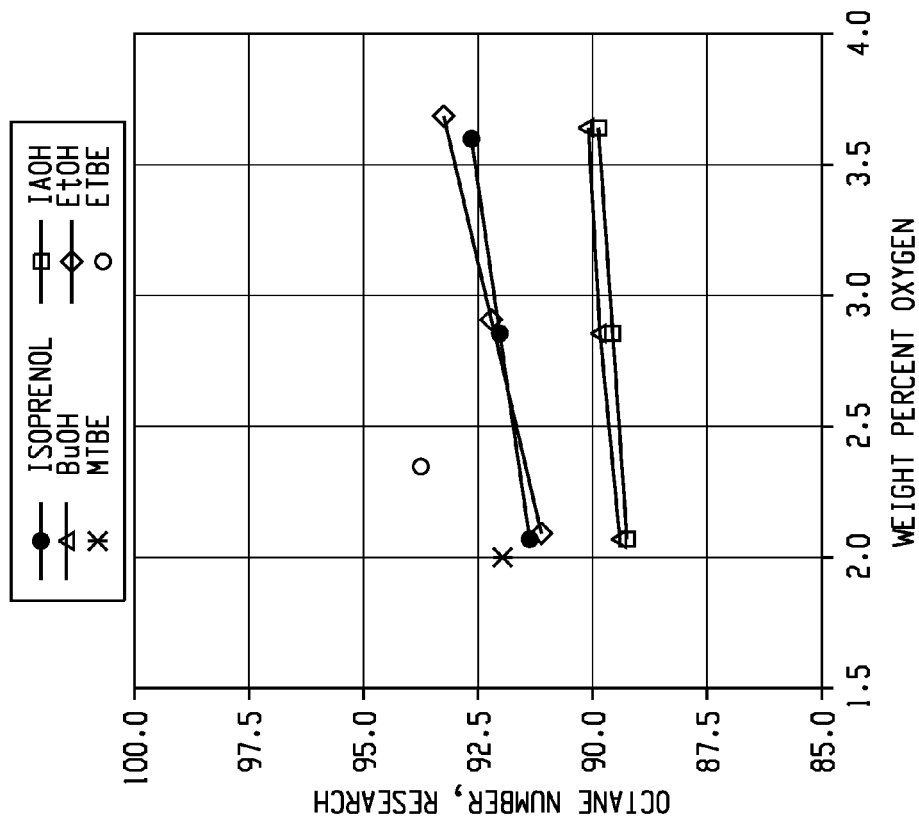
FIG. 10 shows the research octane numbers (RON) of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
Figures 12, 13:
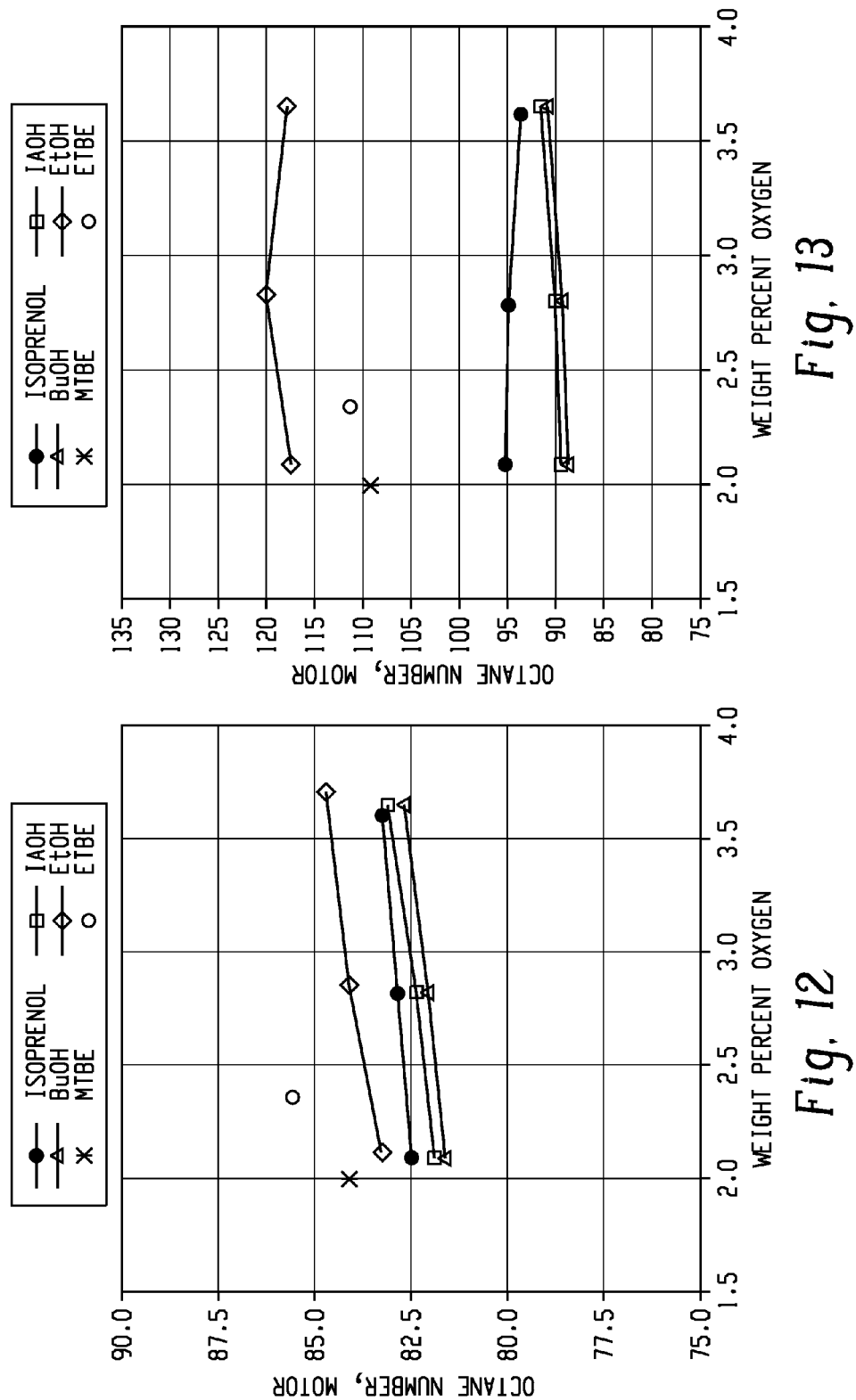
FIG. 12 shows the motor octane numbers (MON) of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
FIG. 13 shows the motor octane numbers (MON) of isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
Figure 15:
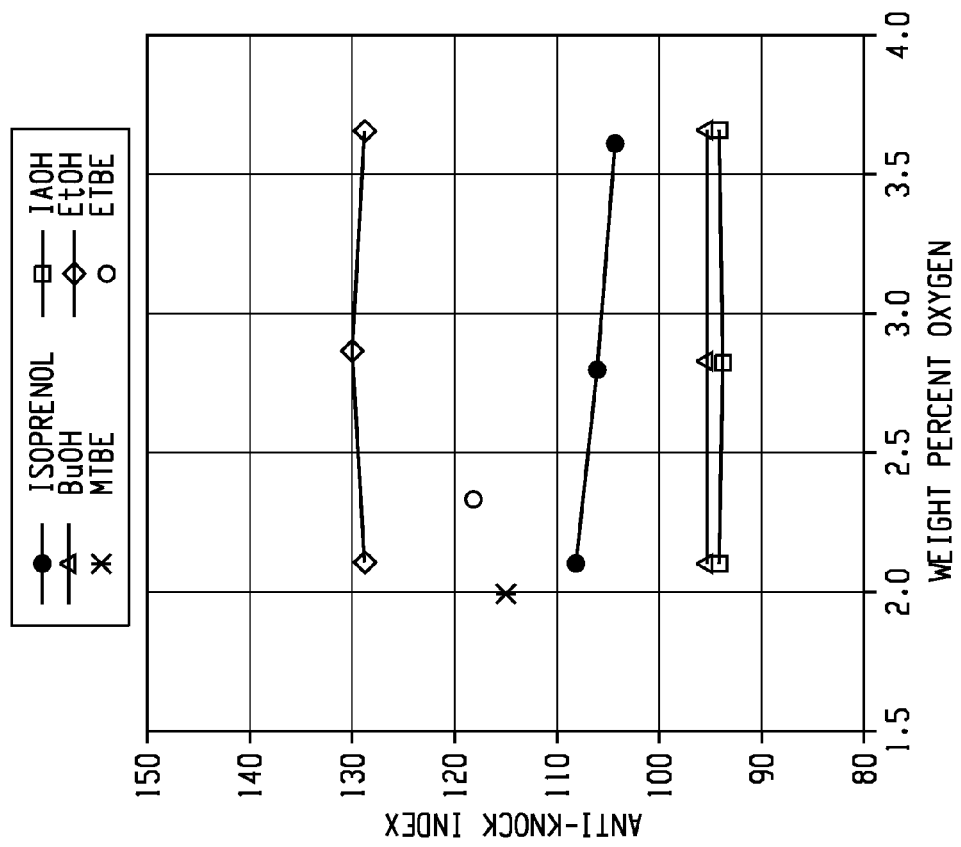
FIG. 15 shows the anti-knock indexes of isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
Figure 14:
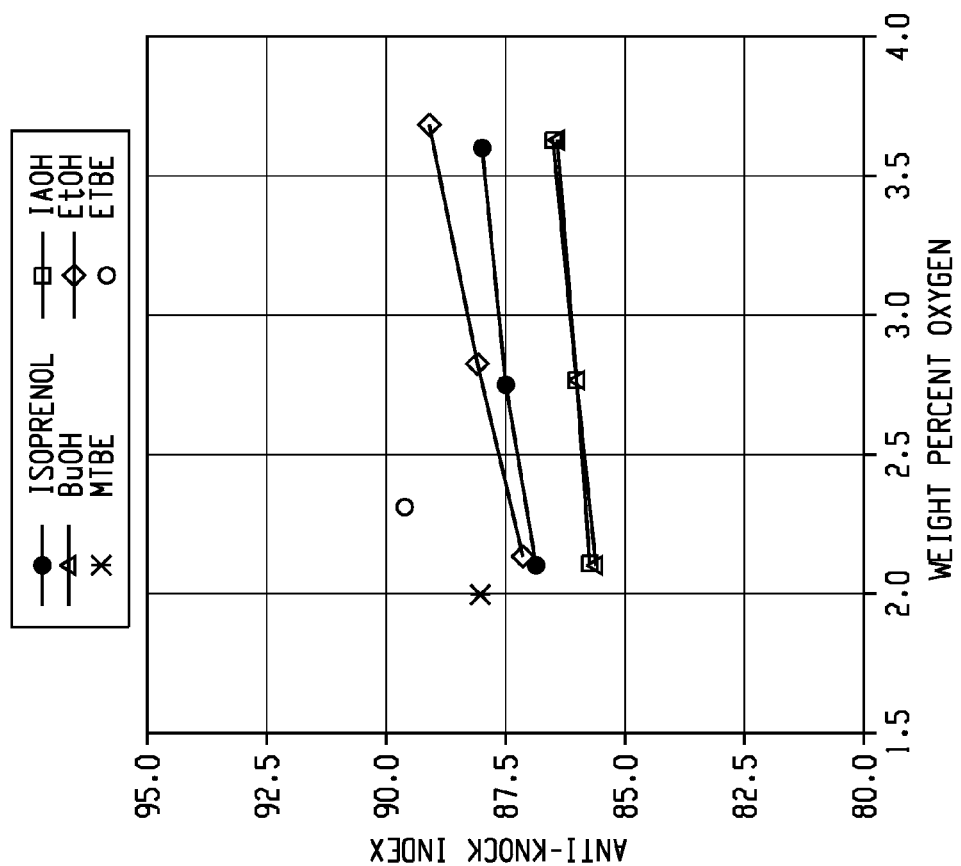
FIG. 14 shows the anti-knock indexes of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
Figure 16:
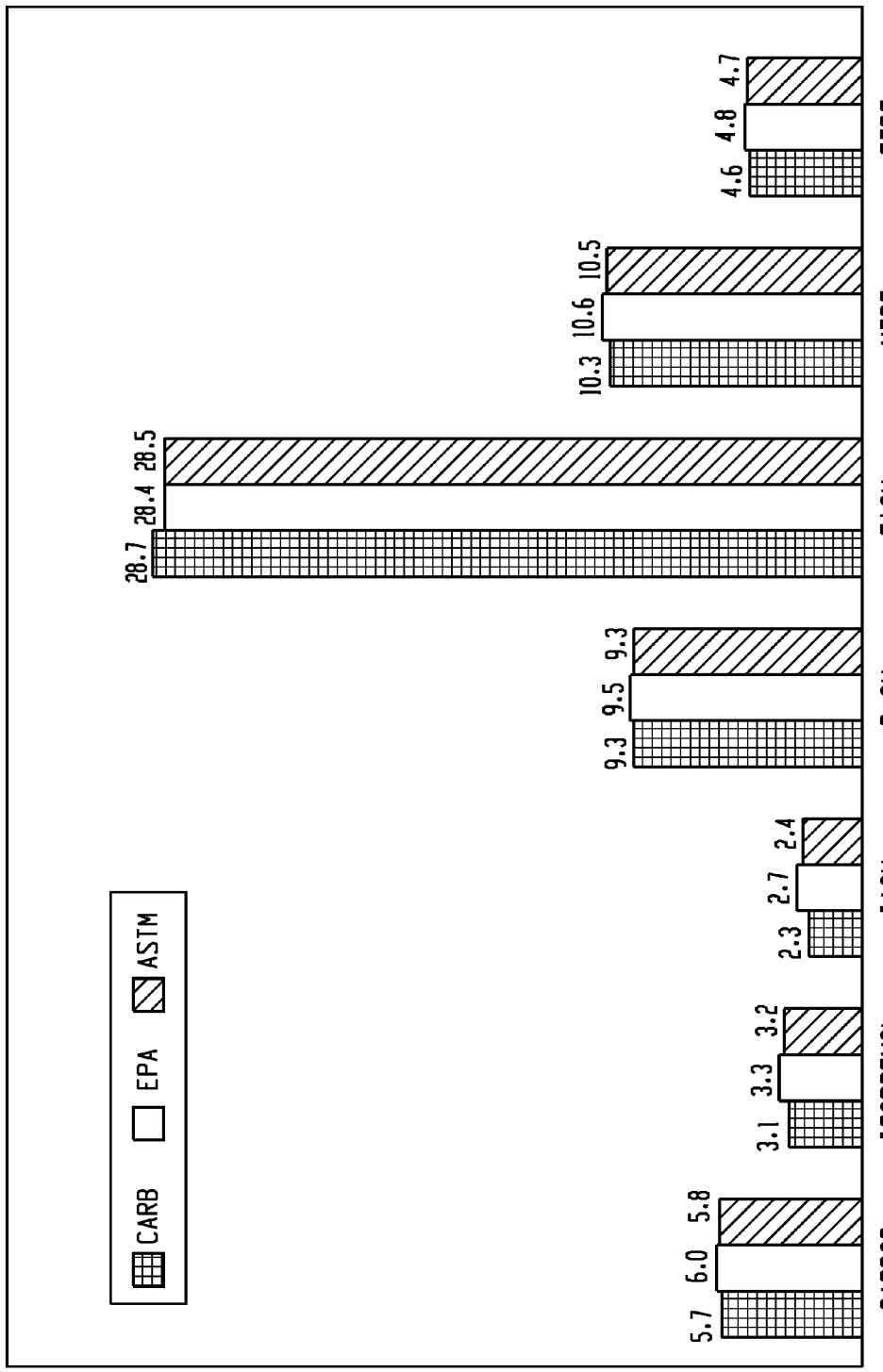
FIG. 16 shows the vapor pressure values of CARBOB, isoprenol, isoamyl alcohol (IAOH), 1-butanol (BuOH), ethanol (EtOH), methyl tertiary-butyl ether (MTBE) and ethyl tertiary-butyl ether (ETBE) respectively at approximately 2 wt. % oxygen content measured according to the CARB (represented by bars with squares), EPA (represented by white bars) and ASTM D 5191 (represented by bars with slant lines) methods.
Figure 19:
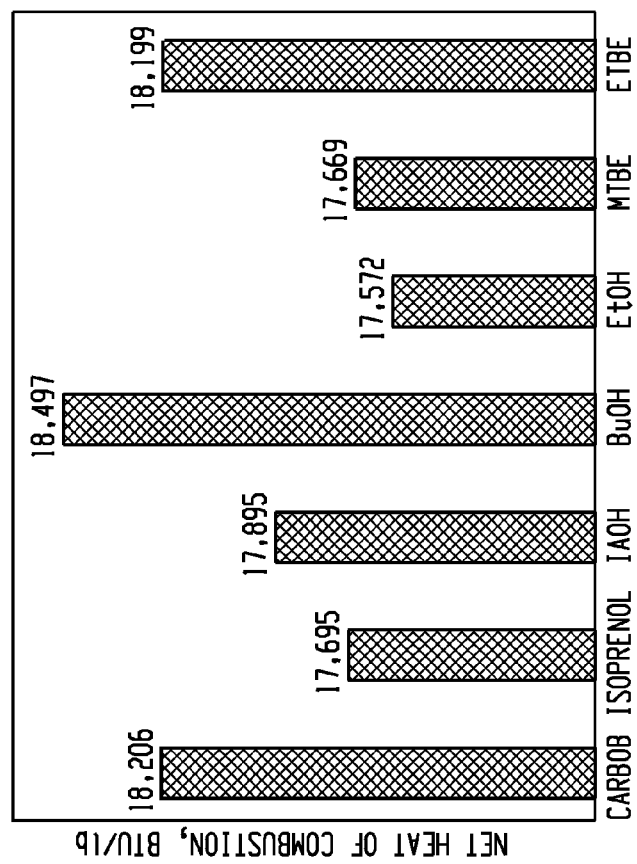
FIG. 19 shows the vapor pressure values of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content measured by the ASTM method.
Figure 20:
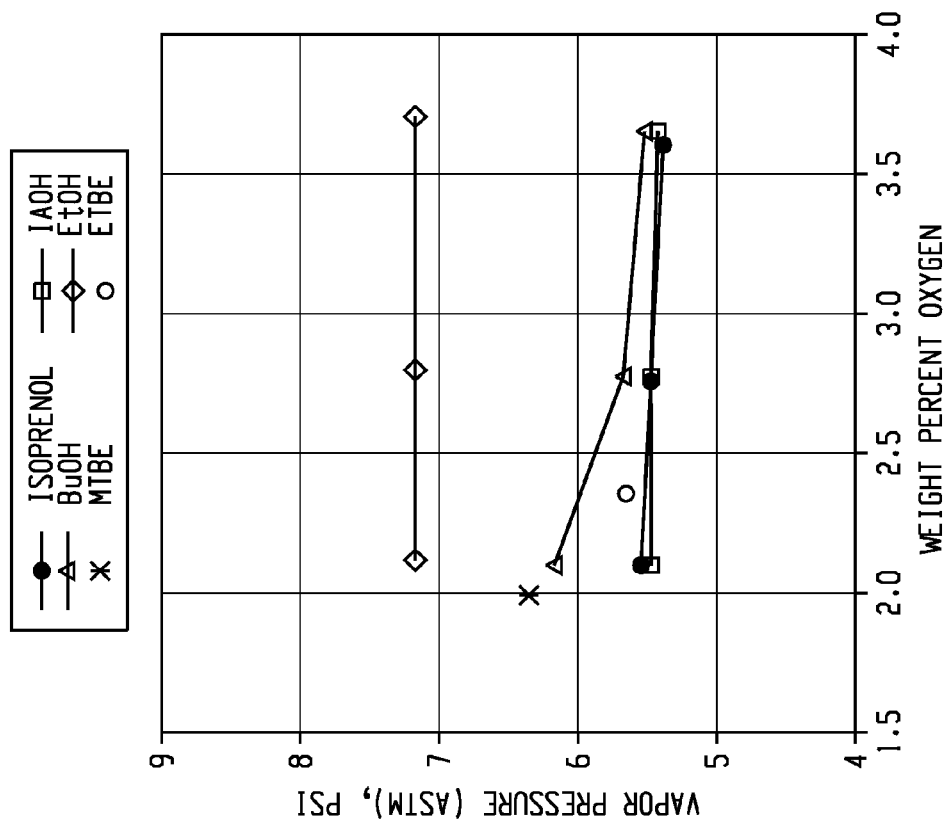
FIG. 20 shows the net heats of combustion of CARBOB, isoprenol, isoamyl alcohol (IAOH), 1-butanol (BuOH), ethanol (EtOH), methyl tertiary-butyl ether (MTBE) and ethyl tertiary-butyl ether (ETBE) respectively at approximately 2 wt. % oxygen content.
Figure 21:
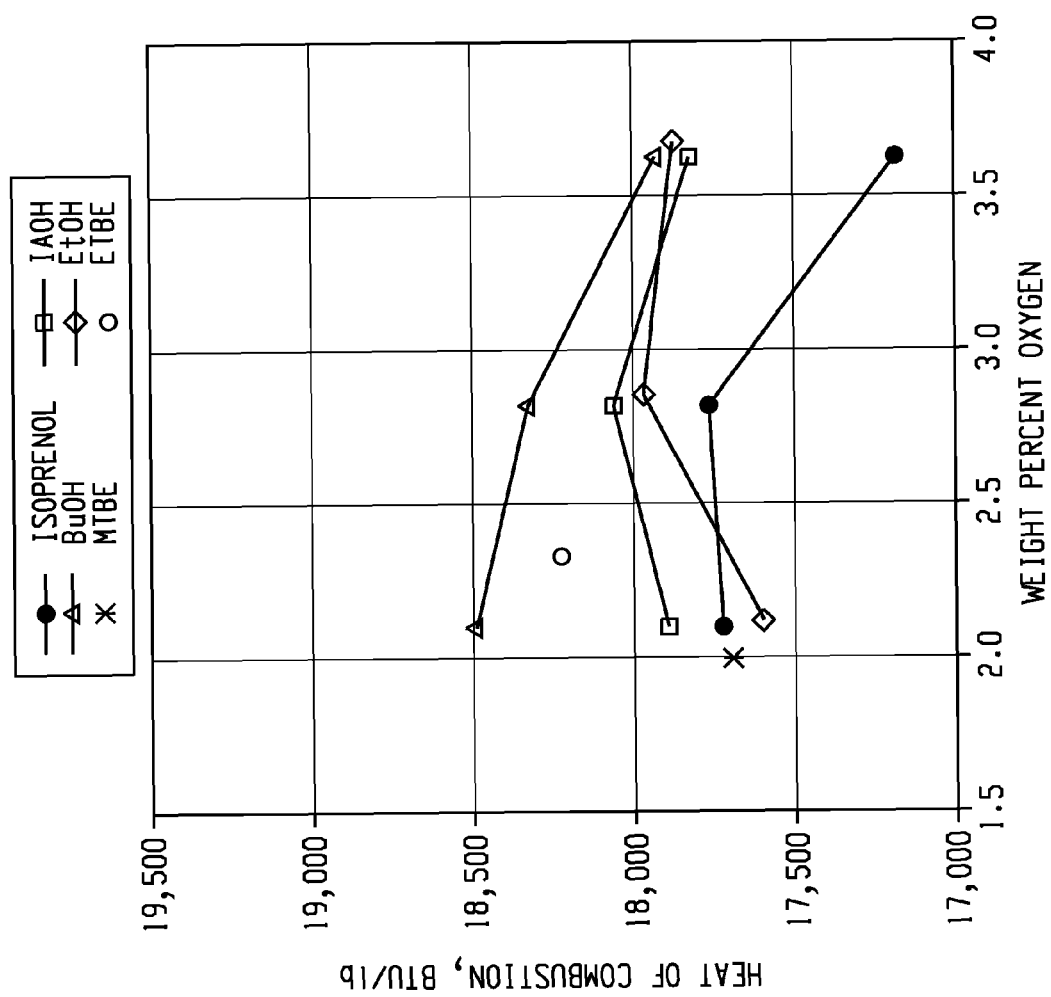
FIG. 21 shows the net heats of combustion of mixtures of CARBOB and isoprenol (represented by solid circles), isoamyl alcohol (IAOH; represented by open squares), 1-butanol (BuOH; represented by open triangles), ethanol (EtOH; represented by open diamonds), methyl tertiary-butyl ether (MTBE; represented by *'s) and ethyl tertiary-butyl ether (ETBE; represented by open circles) respectively at various wt. % oxygen content.
Figure 22:
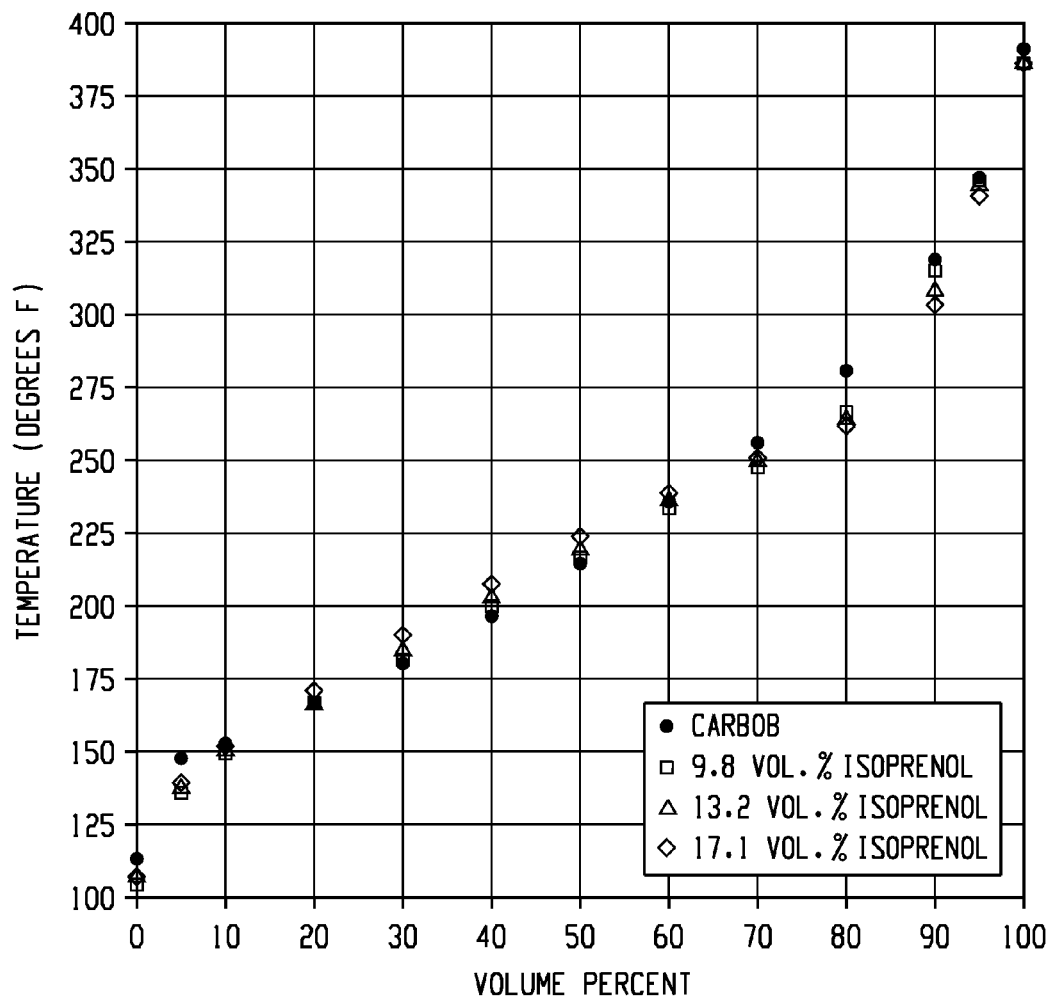
FIG. 22 shows the distillation curves of CARBOB and mixtures of CARBOB and 9.8 vol. % (represented by open squares), 13.2 vol. % (represented by open triangles) and 17.1 vol. % (represented by open diamonds) of isoprenol respectively.
Figure 23:
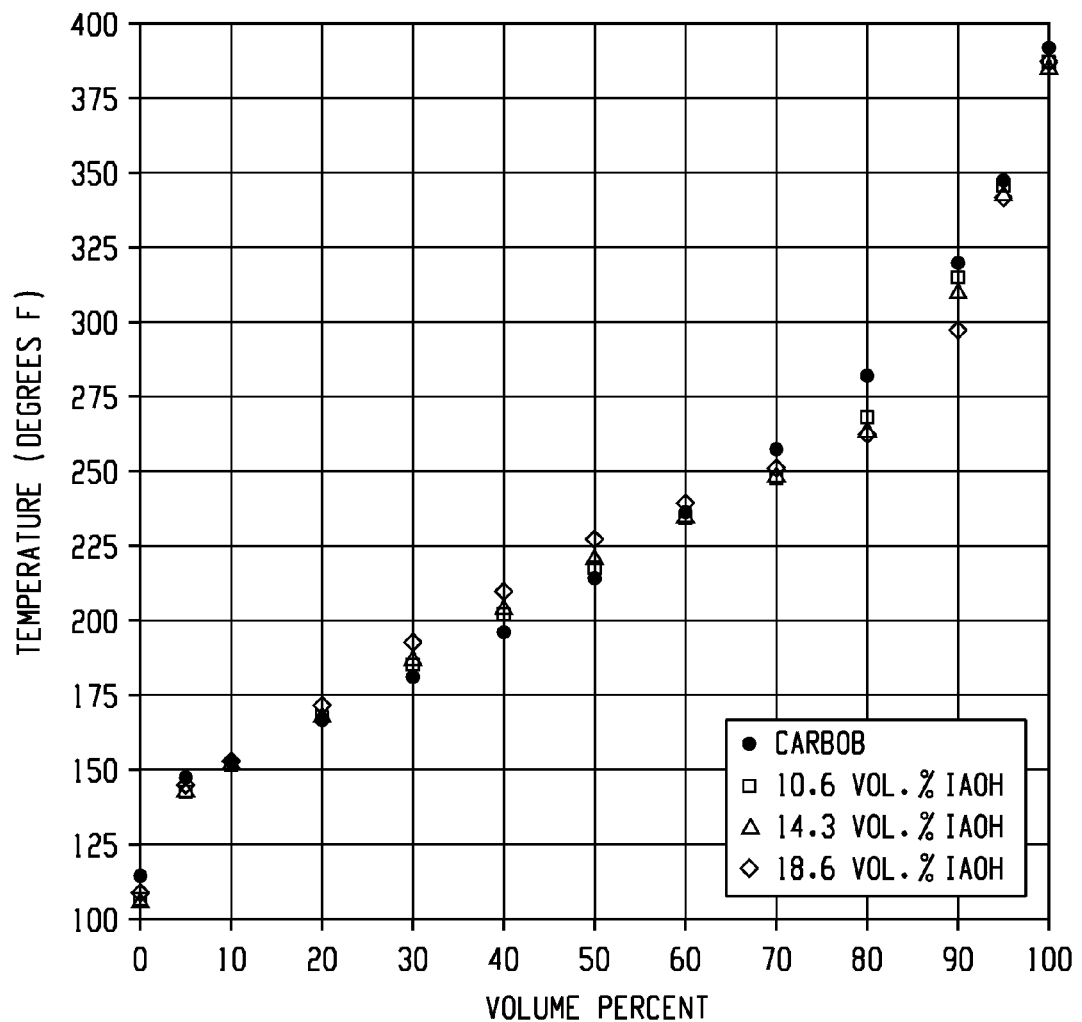
FIG. 23 shows the distillation curves of CARBOB and mixtures of CARBOB and 10.6 vol. % (represented by open squares), 14.3 vol. % (represented by open triangles) and 18.6 vol. % (represented by open diamonds) of isoamyl alcohol respectively.
Figure 24:
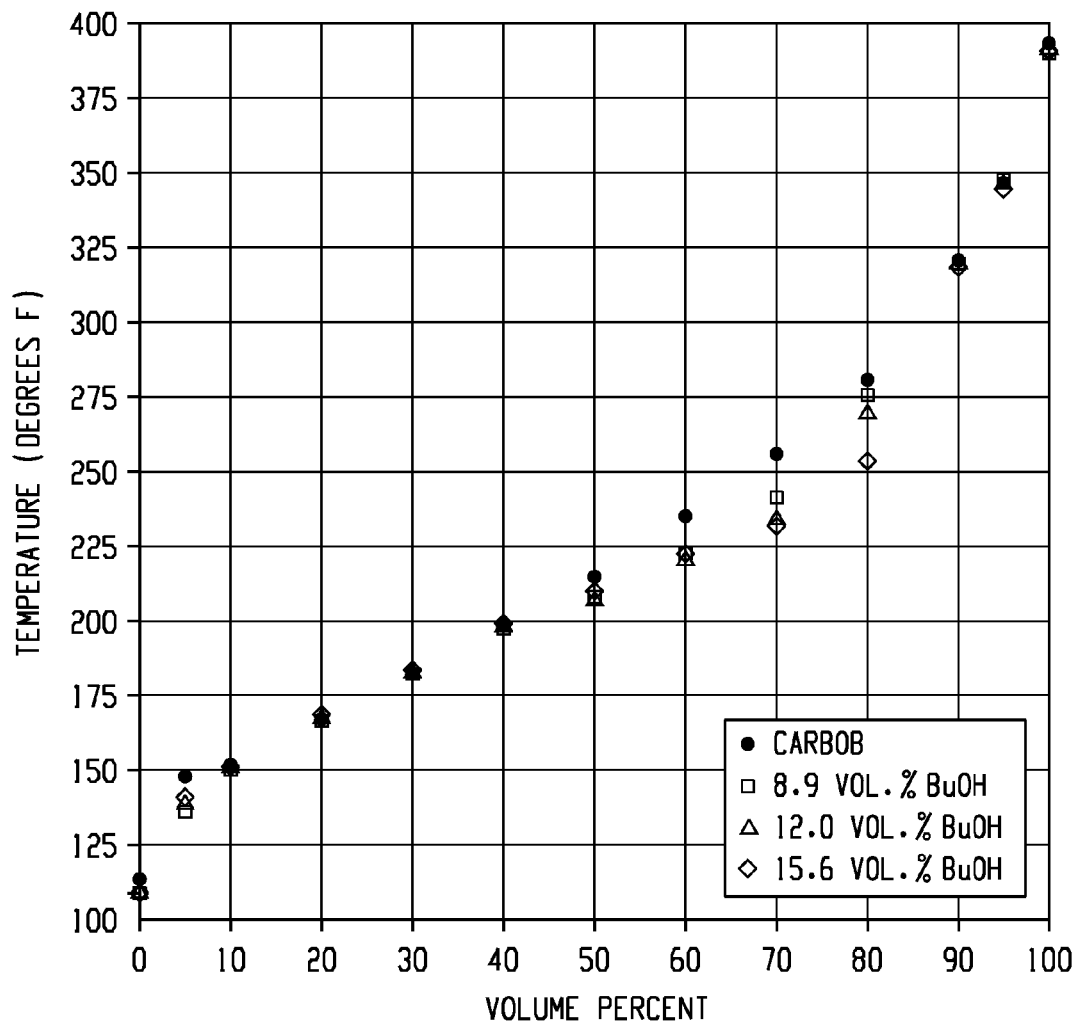
FIG. 24 shows the distillation curves of CARBOB and mixtures of CARBOB and 8.9 vol. % (represented by open squares), 12.0 vol. % (represented by open triangles) and 15.6 vol. % (represented by open diamonds) of 1-butanol respectively.
Figure 25:
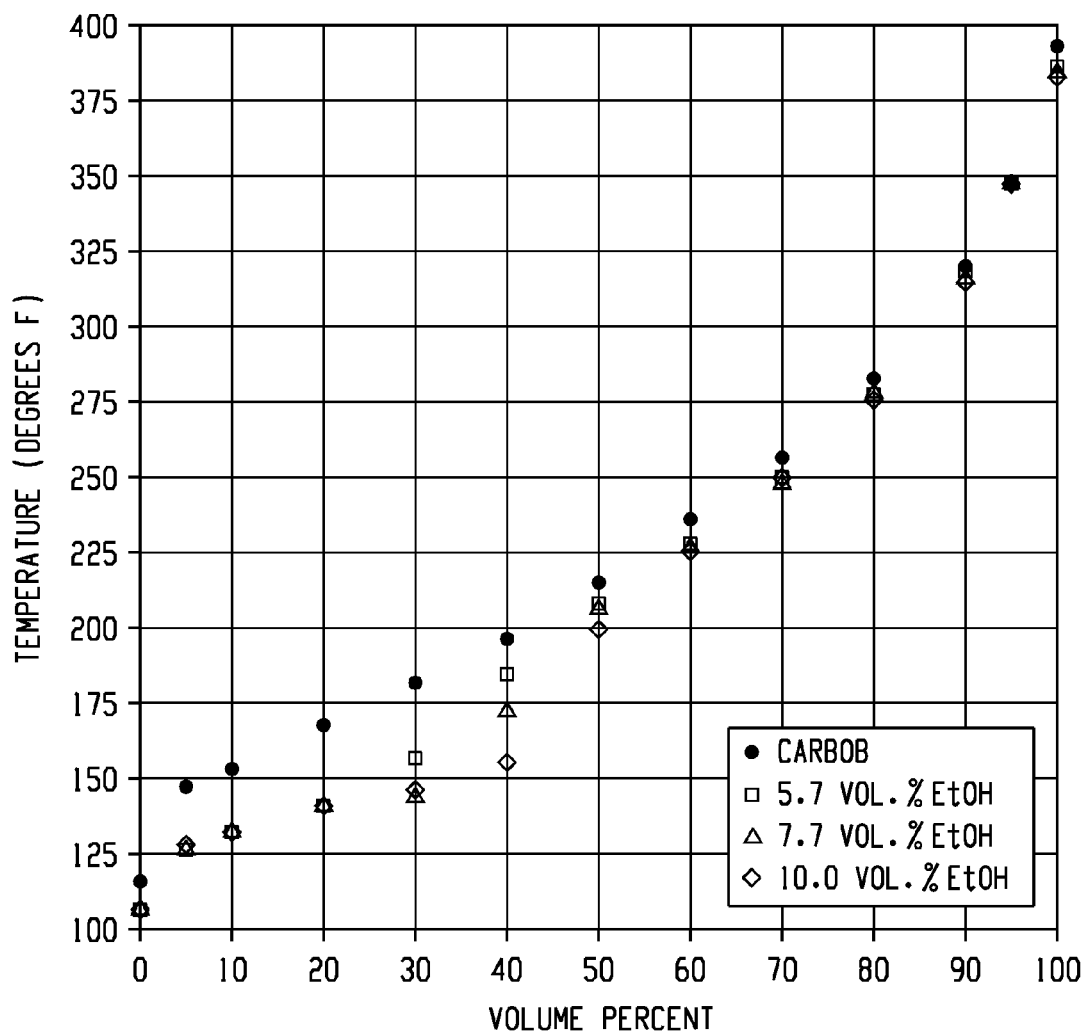
FIG. 25 shows the distillation curves of CARBOB and mixtures of CARBOB and 5.7 vol. % (represented by open squares), 7.7 vol. % (represented by open triangles) and 10.0 vol. % (represented by open diamonds) of ethanol respectively.

FIG. 3 shows relative production levels of 3-methyl-3-buten-1-ol or 3-methyl-2-buten-1-ol by strains DH1 (untransformed control), B286, B287, and B291.

The 3-methyl-3-buten-1-ol and isoamyl alcohol were blended respectively with a California Reformulated Gasoline Blendstock for Oxygen Blending (CARBOB) to form various mixtures having an oxygen content of 2 wt %, 2.7 wt. % or 3.5 wt. %. Similarly, 1-butanol, ethanol, methyl tertiary-butyl ether (MTBE) and ethyl tertiary-butyl ether (ETBE) are also blended respectively with CARBOB to form various mixtures having an oxygen content of 2 wt %, 2.7 wt. % or 3.5 wt. %. The API gravity values, research octane numbers, motor octane numbers, anti-knock indexes, vapor pressure data, net heats of combustion, water tolerance data, and vapor-liquid ratio of the mixtures were tested. The test results are shown in FIGS. 4-25.

The fuel composition disclosed herein can be produced in a cost-effective and environmentally friendly manner. Advantageously, the isoprenoid compounds provided herein can be produced by one or more microorganisms. These isoprenoid compounds can thus provide a renewable source of energy as a substitute for petroleum-based fuel such as gasoline. Further, these isoprenoid compounds can decrease dependence on non-renewable sources of fuel, fuel components and/or fuel additives. In certain embodiments, the present invention encompasses a fuel composition comprising a bioengineered 3-methyl-1-butanol.

As demonstrated above, embodiments of the invention provide various fuel compositions which are particularly useful as jet fuels or missile fuels. While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. For example, the jet fuel compositions disclosed herein need not comprising 3-methyl-1-butanol, 2-methylbutane or a combination thereof. It can comprise any type of hydrocarbons generally suitable for jet fuel applications. It should be noted that the application of the fuel compositions disclosed herein is not limited to gasoline engines; they can be used in any equipment which requires gasoline. Although there are specifications for most gasoline compositions, not all gasoline compositions disclosed herein need to meet all requirements in the specifications. It is noted that the methods for making and using the fuel compositions disclosed herein are described with reference to a number of steps. These steps can be practiced in any sequence. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fuel composition comprising or obtainable from a mixture comprising:
   (a) a $C_5$ isoprenoid compound of formula (Ib) or (Ic):

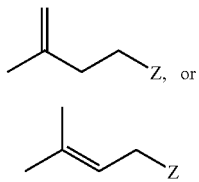

wherein Z is O—R, O—C(=O)R, O—PO(OR)$_2$, O—SO$_2$—OR, PO(OR)$_2$ or SO$_2$—OR; and R is H, alkyl, cycloalkyl, aryl, alkaryl or aralkyl; and
   (b) a fuel additive.

2. The fuel composition of claim 1, wherein the amount of the $C_5$ isoprenoid compound is from about 1% to about 95% by weight or volume, based on the total weight or volume of the fuel composition.

3. The fuel composition of claim 1, wherein Z of formula (Ib) or (Ic) is OH.

4. The fuel composition of claim 1, wherein the $C_5$ isoprenoid compound is according to formula (Ib).

5. The fuel composition of claim 4, wherein Z is OH.

6. The fuel composition of claim 1, wherein the $C_5$ isoprenoid compound is according to formula (Ib).

7. The fuel composition of claim 6, wherein Z is OH.

8. The fuel composition of claim 3, wherein the fuel composition is substantially free of a second alcohol, wherein the second alcohol is not 3-methyl-3-buten-1-ol, 3-methyl-2-buten-1-ol or a combination thereof.

9. The fuel composition of claim 8, wherein the second alcohol is methanol, ethanol, n-propanol, iso-propanol, n-butanol, iso-butanol, tert-butanol, n-pentanol, sec-pentanol, tert-pentanol, n-hexanol, iso-hexanol, sec-hexanol, tert-hexanol, heptanols, octanols, nonanols, decanols or a combination thereof.

10. The fuel composition of claim 1, wherein the fuel composition is substantially free of an aromatic compound.

11. The fuel composition of claim 1 further comprising a petroleum-based fuel in an amount from about 1% to about 95% by weight or volume, based on the total weight or volume of the fuel composition.

12. The fuel composition of claim 11, wherein the petroleum-based fuel is gasoline.

13. The fuel composition of claim 12 wherein the $C_5$ isoprenoid compound is according to formula (Ib) and Z is OH and the $C_5$ isoprenoid compound is present in an amount from about 1% to about 12.5% by volume, based on the total volume of the fuel composition.

14. The fuel composition of claim 1, wherein the fuel additive is selected from the group consisting of oxygenates, antioxidants, thermal stability improvers, cetane improvers, stabilizers, cold flow improvers, combustion improvers, antifoams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof.

15. The fuel composition of claim 1, wherein the amount of the fuel additive is from about 0.1% to about 20% by weight or volume, based on the total weight or volume of the fuel composition.

16. A fuel composition made by a method comprising the steps of:
(a) contacting a cell capable of making a $C_5$ isoprenoid compound of formula (Ib) or (Ic):

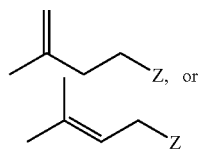

wherein Z is OH with a simple sugar under conditions suitable for making the $C_5$ isoprenoid compound; and
(b) mixing the $C_5$ isoprenoid compound with one or more fuel components or fuel additives to make the fuel composition.

17. A fuel composition comprising a fuel component and a bioengineered $C_5$ isoprenoid compound.

18. A fuel composition produced by preparing 3-methyl-3-buten-1-ol from a mixture comprising a microorganism, and incorporating the 3-methyl-3-buten-1-ol in a fuel.

19. The fuel composition of claim 18, wherein the mixture further comprises a simple sugar.

20. The fuel composition of claim 19, wherein the simple sugar is glucose, galactose, mannose, fructose, ribose or a combination thereof.

* * * * *

SEQUENCE LISTING

```
<160> NUMBER OF SEQ ID NOS: 12

<210> SEQ ID NO 1
<211> LENGTH: 4247
<212> TYPE: DNA
<213> ORGANISM: Artificial Sequence
<220> FEATURE:
<223> OTHER INFORMATION: a template comprising genes from E. coli and S.
      cerevisiae and been used to synthetically generate MevT66 operon

<400> SEQUENCE: 1
gaattcaaag gaggaaaata aaatgaagaa ctgtgtgatt gtttctgcgg tccgcacggc      60
gatcggcagc tttaacggct ctttagcgag cacctctgca atcgatctgg gtgcgacggt     120
cattaaggcc gccattgaac gcgccaaaat cgacagccag cacgttgatg aggtgatcat     180
gggcaatgtg ttacaagccg gcctgggtca aaacccagcg cgtcaagcac tgttaaaatc     240
tggtctggcc gagaccgtgt gtggcttcac cgtcaataag gtttgcggct ctggcctgaa     300
gagcgtggcc ctggcagcac aagcgattca agccggtcag gcacaaagca tcgttgcggg     360
tggcatggag aacatgtctc tggcgccgta cttattagat gccaaagccc gcagcggtta     420
tcgcctgggc gatggtcagg tgtacgacgt catcttacgc gatggcttaa tgtgcgcgac     480
ccacggttac cacatgggta ttacggccga aaacgtggcg aaagaatacg gcattacgcg     540
cgagatgcag gatgaattag cactgcactc tcagcgcaaa gcagcagccg cgatcgagtc     600
tggtgcgttt acggcggaaa tcgtgccagt taacgtggtc acgcgcaaga agacgttcgt     660
tttcagccag gacgagttcc cgaaggcaaa cagcaccgcg gaggccttag gtgccttacg     720
cccagccttt gacaaagcgg gcacggtcac cgccggtaat gcgagcggca tcaatgatgg     780
tgcagcggca ctggtcatca tggaagagag cgccgcatta gcagcgggtc tgacccatt     840 agcgcgcatt aaatcttatg ccagcggcgg cgtcccacca gccctgatgg gcatgggtcc     900
ggtcccagcc acgcaaaaag ccctgcaatt agcgggcctg caactggccg acattgatct     960
gatcgaggcg aacgaggcgt ttgcagcgca gttcctggcg gtgggtaaga atctgggctt    1020
cgacagcgag aaagtcaatg tgaacggtgg cgcgattgcg ttaggccatc cgattggtgc    1080
```

-continued

```
aagcggcgca cgcatcttag tgacgttact gcacgccatg caggcacgcg acaagacctt    1140
aggcctggcg accttatgta ttggtggcgg tcaaggtatc gccatggtga tcgaacgcct    1200
gaactgaaga tctaggagga aagcaaaatg aaactgagca ccaagctgtg ctggtgtggc    1260
atcaagggtc gcctgcgccc acaaaagcag caacagctgc acaacacgaa cctgcaaatg    1320
accgagctga aaagcagaa gacggccgag caaaagaccc gcccgcagaa cgttggcatc    1380
aagggcatcc agatttatat cccgacgcag tgtgtcaacc aatctgagct ggagaaattc    1440
gatggcgtca gccagggtaa gtacaccatc ggcctgggcc agaccaacat gagcttcgtg    1500
aacgaccgtg aggacatcta ttctatgagc ctgacggtgc tgtctaagct gatcaagagc    1560
tacaacatcg acacgaataa gatcggtcgt ctggaggtgg gtacgagac gctgattgac    1620
aagagcaaaa gcgtgaagtc tgtcttaatg cagctgttcg gcgagaacac ggatgtcgag    1680
ggtatcgaca ccctgaacgc gtgttacggc ggcaccaacg cactgttcaa tagcctgaac    1740
tggattgaga gcaacgcctg ggatggccgc gatgcgatcg tcgtgtgcgg cgatatcgcc    1800
atctatgaca agggtgcggc acgtccgacc ggcggtgcag gcaccgttgc gatgtggatt    1860
ggccccggacg caccaattgt cttcgattct gtccgcgcgt cttacatgga gcacgcctac    1920
gactttaca gccggactt cacgagcgaa tacccgtacg tggacggcca cttctctctg    1980
acctgctatg tgaaggcgct ggaccaggtt tataagtctt atagcaaaaa ggcgatttct    2040
aagggcctgg tcagcgaccc ggcaggcagc gacgccctga cgtgctgaa gtatttcgac    2100
tacaacgtgt tccatgtccc gacctgcaaa ttagtgacca atcttatgg ccgcctgtta    2160
tataatgatt tccgtgccaa cccgcagctg ttcccggagg ttgacgccga gctggcgacg    2220
cgtgattacg acgagagcct gaccgacaag aacatcgaga agaccttcgt caacgtcgcg    2280
aagccgttcc acaaagagcg tgtggcccaa agcctgatcg tcccgaccaa cacgggcaac    2340
atgtataccg cgtctgtcta cgcggcattc gcgagcctgc tgaattacgt cggttctgac    2400
gacctgcagg gcaagcgcgt tggcctgttc agctacggta gcggcttagc ggccagcctg    2460
tatagctgca aaattgtcgg cgacgtccag cacatcatca aggagctgga catcaccaac    2520
aagctggcga agcgcatcac cgagacgccg aaagattacg aggcagcgat cgagttacgc    2580
gagaatgcgc atctgaagaa gaacttcaag ccgcaaggta gcatcgagca cctgcagagc    2640
ggcgtctact acctgacgaa cattgacgac aagttccgcc gttcttatga cgtcaaaaag    2700
taactagtag gaggaaaaca tcatggtgct gacgaacaaa accgtcatta gcggcagcaa    2760
ggtgaagtct ctgagcagcg cccaaagctc tagcagcggc ccgtctagca gcagcgagga    2820
ggacgacagc cgtgacattg agtctctgga caagaagatc cgcccgctgg aggagttaga    2880
ggccctgctg agcagcggca acaccaagca gctgaagaac aaggaagttg cagcgctggt    2940
gatccacggt aagctgccac tgtatgcgct ggaaaagaaa ctgggcgata cgacgcgtgc    3000
ggtcgcggtg cgtcgcaaag ccttaagcat cttagcggag gccccggtgt tagccagcga    3060
ccgcctgccg tacaagaact acgactacga ccgcgtgttt ggcgcgtgct gcgagaatgt    3120
cattggctac atgccgttac cggttggtgt gatcggcccg ctggtcattg atggcacgag    3180
ctatcacatt ccaatggcga ccacggaagg ttgcttagtc gccagcgcca tgcgtggctg    3240
taaggcgatt aacgccggcg gtgcgcgac gaccgtgtta accaaggatg gtatgacgcg    3300
cggtccggtc gtccgcttcc caacgctgaa gcgcagcggc gcgtgtaaga tttggctgga    3360
ttctgaggag ggccaaaacg cgatcaagaa agccttcaac tctacgagcc gtttcgcgcg    3420
```

```
tttacagcat atccagacct gcctggccgg cgacctgctg ttcatgcgct tccgcaccac    3480
cacgggcgat gcgatgggca tgaacatgat cagcaagggc gtcgaatata gcctgaaaca    3540
aatggtggaa gaatatggct gggaggacat ggaggttgtc tctgtgagcg gcaactattg    3600
caccgacaag aagccggcag ccattaactg gattgagggt cgcggcaaaa gcgtcgtggc    3660
agaagcgacc atcccaggcg acgtggtccg taaggttctg aagagcgacg tcagcgccct    3720
ggttgagtta aatatcgcga aaaacctggt cggcagcgcg atggcgggca cgtgggtgg     3780 ctttaacgca catgcagcga atctggttac ggcggttttc ttagccttag gtcaggaccc    3840
agcccaaaat gtcgagagca gcaactgcat taccttaatg aaagaggttg acggtgacct    3900
gcgcatcagc gtttctatgc cgtctatcga ggtcggcacg atcggcggcg gcaccgtttt    3960
agaaccgcaa ggtgcgatgc tggatctgct gggcgtgcgc ggcccacatg caacggcccc    4020
aggcaccaat gcccgccaac tggcccgtat cgtggcctgc gcggttctgg cgggtgagct    4080
gagcctgtgc gccgcattag ccgcgggcca tttagttcaa tctcacatga cccacaaccg    4140
caagccggca gaaccaacca agccaaataa cctggacgca accgacatta accgtctgaa    4200
ggatggcagc gtcacgtgca ttaaaagctg agcatgctac taagctt               4247

<210> SEQ ID NO 2
<211> LENGTH: 49
<212> TYPE: DNA
<213> ORGANISM: Artificial Sequence
<220> FEATURE:
<223> OTHER INFORMATION: Primer 4-49 mvaA SpeI

<400> SEQUENCE: 2
gctactagta ggaggaaaac atcatgcaaa gtttagataa gaatttccg                49

<210> SEQ ID NO 3
<211> LENGTH: 39
<212> TYPE: DNA
<213> ORGANISM: Artificial Sequence
<220> FEATURE:
<223> OTHER INFORMATION: Primer 4-49 mvaAR XbaI

<400> SEQUENCE: 3
gcttctagac tattgttgtc taatttcttg taaaatgcg                           39

<210> SEQ ID NO 4
<211> LENGTH: 55
<212> TYPE: DNA
<213> ORGANISM: Artificial Sequence
<220> FEATURE:
<223> OTHER INFORMATION: Primer HMGS 5' Sa mvaS-S

<400> SEQUENCE: 4
gaactgaaga tctaggagga aagcaaaatg acaataggta tcgacaaaat aaact         55

<210> SEQ ID NO 5
<211> LENGTH: 52
<212> TYPE: DNA
<213> ORGANISM: Artificial Sequence
<220> FEATURE:
<223> OTHER INFORMATION: Primer HMGS 3' Sa mvaS-AS

<400> SEQUENCE: 5
ttgcatgatg ttttcctcct actagttact ctggtctgtg atattcgcga ac            52

<210> SEQ ID NO 6
<211> LENGTH: 42
```

-continued

```
<212> TYPE: DNA
<213> ORGANISM: Artificial Sequence
<220> FEATURE:
<223> OTHER INFORMATION: Primer 19-25 atoB SfiI-S

<400> SEQUENCE: 6
gctaggccat cctggccatg aagaactgtg tgattgtttc tg                          42

<210> SEQ ID NO 7
<211> LENGTH: 33
<212> TYPE: DNA
<213> ORGANISM: Artificial Sequence
<220> FEATURE:
<223> OTHER INFORMATION: Primer 19-25 mvaA-AsiSI-AS

<400> SEQUENCE: 7
gcttgcgatc gccggcggat ttgtcctact cag                                    33

<210> SEQ ID NO 8
<211> LENGTH: 35
<212> TYPE: DNA
<213> ORGANISM: Artificial Sequence
<220> FEATURE:
<223> OTHER INFORMATION: Primer 9-70C

<400> SEQUENCE: 8
ccacctcgag atgtcattac cgttcttaac ttctg                                  35

<210> SEQ ID NO 9
<211> LENGTH: 41
<212> TYPE: DNA
<213> ORGANISM: Artificial Sequence
<220> FEATURE:
<223> OTHER INFORMATION: Primer 26-39B

<400> SEQUENCE: 9
tggtggagct cttatttaag ctgggtaaat gcagataatc g                           41

<210> SEQ ID NO 10
<211> LENGTH: 39
<212> TYPE: DNA
<213> ORGANISM: Artificial sequence
<220> FEATURE:
<223> OTHER INFORMATION: Primer 26-39A

<400> SEQUENCE: 10
ttcttgagct cttattcctt tggtagacca gtctttgcg                              39

<210> SEQ ID NO 11
<211> LENGTH: 817
<212> TYPE: DNA
<213> ORGANISM: Bacillus subtilis

<400> SEQUENCE: 11
gtgcacactc ctttttagg ctttgtattg accgtaatat aaaggagcta agtttcaac         60 ttttatggct ttgagatcca atctttcaca tattgaaatg tgcgtccata ctctttaac       120 ttcgctcgaa tttcccatgc ttttccgact aagacaacac cttttggcat gcggtgcact     180
ttcacgaaga agccccctt tgctctagta tgataaatg tatggggcat catatagaga       240
cagaacggga gatgaagaaa tgaaatcatt agaagaaaaa acaattgcca agaacagat     300 ttttcgggt aaagtcattg atctttatgt cgaggatgta gagctgccaa acggcaaagc     360
cagtaaacgt gaaattgtga acacccctgg agctgtagcg gtactagccg tcacagatga   420
```

-continued

```
agggaaaatc atcatggtca aacaattccg taagccgctt gagcggacga tcgttgaaat    480
tccggccggt aagcttgaaa aaggtgagga gccggagtat acggcacttc gggaacttga    540
agaggaaacc ggttatacag caaaaaaact gacaaaaata actgcgtttt atacatcacc    600
cggatttgca gatgaaatcg ttcacgtttt tcttgctgag gagctttctg tgcttgaaga    660
aaaacgggag cttgatgagg acgagtttgt tgaagtgatg gaggtgacgc ttgaagatgc    720
gctaaagctg gttgaatcgc gtgaagtata tgatgctaaa acagcctacg cgattcagta    780
tcttcagctg aaagaagcgc tccaagcaca aaaatga                             817

<210> SEQ ID NO 12
<211> LENGTH: 582
<212> TYPE: DNA
<213> ORGANISM: Bacillus subtilis

<400> SEQUENCE: 12
atgacagccg tttgtttagt aagacatgga gaaaccgatt ggaacctgca gcaaaaatgc    60
caaggcaaaa ccgatatccc gctaaacgca acaggtgaac gccaagcaag agaaaccgga    120
gaatatgtaa aggactttc ttgggatatt attgtgacga gcccgctgaa aagagcgaaa    180
agaaccgcgg aaattattaa tgaatatctg catcttccga tagtcgagat ggatgatttt    240
aaggaacgcg attacggcga cgcggagggc atgccgctgg aggaacggac aaagcgctat    300
ccagataaca tctatccgaa tatggaaacc ttagaagaac tcactgacag gctgatgggc    360
ggtttggcaa aagtgaatca ggcgtatcca aacaagaagg tgctgatcgt ggcgcacggt    420
gcggcaattc acgccctgct gacagaaata tccggcggtg acccggagct tcaaagcacc    480
cgtctcgtca acgcctgcct cagcaacatt gaatttgcag aagaaaaatg gcggataaaa    540
gactataata tcaacagcca cttatccggc tttatcaaat aa                      582
```